(12) United States Patent
Raines

(10) Patent No.: US 11,098,017 B2
(45) Date of Patent: Aug. 24, 2021

(54) COMPOUNDS FOR TREATING DISORDERS ASSOCIATED WITH ABNORMAL STEROIDOGENESIS

(71) Applicant: The General Hospital Corporation, Boston, MA (US)

(72) Inventor: Douglas Raines, Wayland, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/651,248

(22) PCT Filed: May 17, 2018

(86) PCT No.: PCT/US2018/033209
§ 371 (c)(1),
(2) Date: Mar. 26, 2020

(87) PCT Pub. No.: WO2019/067021
PCT Pub. Date: Apr. 4, 2019

(65) Prior Publication Data
US 2020/0277264 A1 Sep. 3, 2020

Related U.S. Application Data

(60) Provisional application No. 62/564,448, filed on Sep. 28, 2017.

(51) Int. Cl.
*C07D 233/90* (2006.01)
*A61P 5/00* (2006.01)

(52) U.S. Cl.
CPC .............. *C07D 233/90* (2013.01); *A61P 5/00* (2018.01)

(58) Field of Classification Search
CPC .................................................. C07D 233/90
See application file for complete search history.

(56) References Cited

U.S. PATENT DOCUMENTS

| 2005/0033060 | A1 | 2/2005 | Zolle | |
|---|---|---|---|---|
| 2015/0328341 | A1 | 11/2015 | Allolio et al. | |
| 2016/0108047 | A1* | 4/2016 | Blank ................. | C07D 471/04 514/234.2 |
| 2016/0108048 | A1 | 4/2016 | Coburn et al. | |

OTHER PUBLICATIONS

Alexandraki et al., "Long-term remission and recurrence rates in Cushing's disease: predictive factors in a single-centre study," Eur. J. Endocrinol., Mar. 2013, 168(4):639-648.
Allolio et al., "Effect of a single bolus of etomidate upon eight major corticosteroid hormones and plasma ACTH," Clin. Endocrinol., Mar. 1985, 22(3):281-286.
Ambrogio & Cavagnini., "Role of "old" pharmacological agents in the treatment of Cushing's syndrome," J. Endocrinol. Invest., Sep. 2016, 39(9):957-965.
Atkinson et al., "Long-term remission rates after pituitary surgery for Cushing's disease: the need for long-term surveillance," Clin. Endocrinol., Nov. 2005, 63(5):549-559.
Belelli et al., "The in vitro and in vivo enantioselectivity of etomidate implicates the GABAA receptor in general anaesthesia," Neuropharmacology, Jul. 2003, 45(1):57-71.
Campagna et al., "Advancing Novel AnestheticsPharmacodynamic and Pharmacokinetic Studies of Cyclopropyl-methoxycarbonyl Metomidate in Dogs," Anesthesiology, Dec. 2014, 121(6):1203-1216.
Cotten et al., "Cathoetomidate: A Pyrrole Analog of Etomidate Designed Not to Suppress Adrenocortical Function," Anesthesiology, Mar. 2010, 112(3):637-644.
Cotten et al., "Methoxycarbonyl-etomidate: A Novel Rapidly Metabolized and Ultra-short-acting Etomidate Analogue that Does Not Produce Prolonged Adrenocortical Suppression," Anesthesiology, Aug. 2009, 111(2):240-249.
Crozier et al., "Relation of the inhibition of cortisol synthesis in vivo to plasma etomidate concentrations," Der Anaesthesist, May 1988, 37(5):337-339.
Cuevas-Ramos & Fleseriu, "Treatment of Cushing's disease: a mechanistic update," J Endocrinol., Nov. 2014, 223(2):R19-39.
Daniel and Newell-Price., "Therapy of endocrine disease: steroidogenesis enzyme inhibitors in Cushing's syndrome," Eur. J. Endocrinol., Jun. 2015, 172(6):R263-280.
Dimopoulou et al., "Long-term remission and recurrence rates after first and second transsphenoidal surgery for Cushing's disease: care reality in the Munich Metropolitan Region," Eur. J. Endocrinol., Feb. 2014, 170(2):283-292.
Engelhardt & Weber., "Therapy of Cushing's syndrome with steroid biosynthesis inhibitors," J. Steroid Biochem. Mol. Biol., Jun. 1994, 49(4-6):261-267.
Fleseriu and Castinetti., "Updates on the role of adrenal steroidogenesis inhibitors in Cushing's syndrome: a focus on novel therapies," Pituitary, Dec. 2016, 19(6):643-653.
Fleseriu et al., "Second-line treatment for Cushing's disease when initial pituitary surgery is unsuccessful," Curr. Opin. Endocrinol. Diabetes Obes., Aug. 2007, 14(4):323-328.
Forman, "Clinical and molecular pharmacology of etomidate," Anesthesiology, Mar. 2011, 114(3):695-707.
Franks, "Molecular targets underlying general anaesthesia," Br. J. Pharmacol., Jan. 2006, 147(Suppl 1):S72-81.
Fly & Griffiths, "The inhibition by etomidate of the 11β-hydroxylation of cortisol," Clin. Endocrinol., May 1984, 20(5):625-629.
Gadelha & Neto., "Efficacy of medical treatment in Cushing's disease: a systematic review," Clin. Endocrinol. (Oxf)., Jan. 2014, 80(1):1-12.
Godefroi et al., "DL-1-(1-arylalkyl) imidazole-5-carboxylate esters. A novel type of hypnotic agents," Journal of Medicinal Chemistry, Mar. 1965, Mar. 1965, 8(2):220-223.
Jong et al., "Etomidate Suppresses Adrenocortical Function by Inhibition of 1 1β-Hydroxylation," J. Clin. Endocrinol. Metab., Dec. 1984, 59(6):1143-1147.

(Continued)

*Primary Examiner* — Shawquia Jackson
(74) *Attorney, Agent, or Firm* — Fish & Richardson P.C.

(57) ABSTRACT

The present application provides compounds useful for treating disorders associated with abnormal steroidogenesis. Methods of treating disorders associated with abnormal steroidogenesis, methods of inhibiting 11β-hydroxylase activity, and pharmaceutical compositions comprising the compounds are also provided.

20 Claims, 10 Drawing Sheets

(56) References Cited

OTHER PUBLICATIONS

Jurd et al., "General anesthetic actions in vivo strongly attenuated by a point mutation in the GABAA receptor β3 subunit," Faseb. J., Feb. 2003, 17(2):250-252.
Lacroix et al., "Cushing's syndrome," Lancet, Aug. 2015, 386(9996):913-927.
Lambert et al., "On the assessment of the in vitro biopotency and site(s) of action of drugs affecting adrenal steroidogenesis," Ann. Clin. Biochem., Apr. 1986, 23(Pt 3):225-229.
Lamberts et al., "Differential effects of the imidazole derivatives etomidate, ketoconazole and miconazole and of metyrapone on the secretion of cortisol and its precursors by human adrenocortical cells," J. Pharmacol. Exp. Ther., Jan. 1987, 240(1):259-264.
Patil et al., "Late recurrences of Cushing's disease afterinitial successful transsphenoidal surgery," J. Clin. Endocrinol. Metab., 2008, 93(2):358-362.
PCT International Preliminary Report on Patentability in International Appln. No. PCT/US2018/33209, dated Mar. 31, 2020, 7 pages.
PCT International Search Report and Written Opinion in International Appln. No. PCT/US18/33209, dated Sep. 25, 2018, 10 pages.
Pejo et al., "Analogues of Etomidate Modifications around Etomidate's Chiral Carbon and the Impact on in Vitro and in Vivo Pharmacology," Anesthesiology, Aug. 2014, 121(2):290-301.
Pejo et al., "In vivo and in vitro pharmacological studies of methoxycarbonyl-cathoetomidate," Anesth. Analg., Aug. 2012, 115(2):297-304.
Pejo et al., "Sedative-hypnotic binding to 11β-hydroxylase," Anesthesiology, Nov. 2016, 125(5):943-951.
Pivonello et al., "Complications of Cushing's syndrome:state of the art," Lancet Diabetes Endocrinol., May 2016, 4(7):611-629.
Pivonello et al., "Cushing's disease: the burden of illness," Endocrine, Apr. 2017, 56(1):10-18.
Pivonello et al., "Cushing's disease," Endocr. Rev., Aug. 2015, 36(4):385-486.
Preda et al., "Etomidate in the management of hypercortisolaemia in Cushing's syndrome: a review," Eur. J. Endocrinol., Aug. 2012, 167(2):137-143.
Pubmed Compound Summary for CID 424879, 'Methyl 3-(1-naphthalen-1-ylethyl)imidazole-4-carboxylate', Mar. 26, 2005, 7 pages.
Shanmugasundararaj et al., "Carboetomidate: An analog of etomidate that interacts weakly with 11β-hydroxylase," Anesth. Analg., Jun. 2013, 116(6):1249-1256.
Tritos & Biller, "Medical management of Cushing's disease," J. Neurooncol., May 2014, 117(3):407-414.
Tritos and Biller, "Cushing's disease," Handb. Clin. Neurol., Jan. 2014, 124:221-234.
Waud, "On biological assays involving quantal responses," J. Pharmacol. Exp. Ther., Dec. 1972, 183(3):577-607.

* cited by examiner

COMPOUNDS FOR TREATING DISORDERS ASSOCIATED WITH ABNORMAL STEROIDOGENESIS

CROSS-REFERENCE TO RELATED APPLICATIONS

This application is a § 371 National Stage Application of PCT/US2018/033209, filed May 17, 2018, which claims the benefit of U.S. Provisional Application Ser. No. 62/564,448, filed Sep. 28, 2017, the disclosure of which is incorporated herein by reference in its entirety.

FEDERALLY SPONSORED RESEARCH OR DEVELOPMENT

This invention was made with Government support under Grant Nos. GM087316 and GM58448 awarded by the National Institutes of Health. The Government has certain rights in the invention.

TECHNICAL FIELD

The present application provides compounds useful for treating disorders associated with abnormal steroidogenesis. The compounds provided herein are particularly useful for administration at therapeutically effective amounts such that the subject exhibits minimal or no sedative effects (e.g., the subject does not exhibit a loss of righting reflex and/or loss of consciousness).

BACKGROUND

Cushing's Syndrome is characterized by the overproduction of adrenocortical steroids and manifested by a variety of signs and symptoms of hypercortisolemia including hypertension, diabetes, immunosuppression, water retention, depression, poor wound healing, and cognitive impairment (see e.g., Tritos and Biller, *Handb. Clin. Neurol.* 2014, 124:221-234; Lacroix et al., *Lancet,* 2015, 386:913-927); Pivonello et al., *Lancet Diabetes Endocrinol.* 2016, 4:611-629; Pivonello et al., *Endocrine,* 2017, 56:10-18). When poorly controlled, it is associated with significant morbidity (e.g., coronary artery disease and stroke) and increased mortality. It is most commonly caused by an ACTH-secreting pituitary tumor that stimulates steroid production by the adrenal gland (i.e., Cushing's Disease), but can also be the result of ACTH secretion by neuroendocrine tumors, or adrenocortical adenomas or hyperplasia. Although surgery is typically the first line of therapy for patients with Cushing's Syndrome, medical treatment is often necessary due to post-surgical local recurrence or metastatic disease (see e.g., Atkinson et al., *Clin. Endocrinol.* (Oxf). 2005, 63:549-559; Fleseriu et al., *Curr. Opin. Endocrinol. Diabetes Obes.,* 2007, 14:323-328; Patil et al., *J. Clin. Endocrinol. Metab.,* 2008, 93:358-362; Alexandraki et al., *Eur. J. Endocrinol.,* 2013, 168:639-648; Dimopoulou et al., *Eur. J. Endocrinol.* 2014, 170:283-292; Pivonello et al., *Endocr. Rev.* 2015, 36:385-486). Medical treatment may also be instituted. For example, while awaiting the effects of radiation therapy or preoperatively to reduce the risk of surgical complications (see e.g., Cuevas-Ramos and Fleseriu, *J Endocrinol.* 2014, 223:R19-39; Fleseriu and Castinetti, Pituitary, 2016, 19:643-653). Steroidogenesis inhibitors, which reduce steroid synthesis by reversibly inhibiting the function of one or more enzymes in the cortisol biosynthetic pathway, are useful in medical treatments of Cushing's Syndrome (see e.g., Daniel and Newell-Price, *Eur. J. Endocrinol.,* 2015, 172:R263-280).

SUMMARY

The present application provides, inter alia, a compound of Formula Ia:

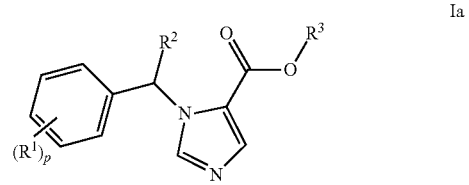

or a pharmaceutically acceptable salt thereof, wherein:
each $R^1$ is independently selected from the group consisting of $C_{1-6}$ alkoxy;
or, alternatively, two adjacent $R^1$ groups, together with the carbon atoms to which they are attached, form an aryl ring having 6 to 10 ring carbon atoms;
$R^2$ is $C_{1-4}$ alkyl;
$R^3$ is $C_{1-4}$ alkyl; and
p is 2 or 3.
In some embodiments, p is 2.
In some embodiments, each $R^1$ is methoxy. In some embodiments, each $R^1$ is methoxy, and p is 2.
In some embodiments, two adjacent $R^1$ groups, together with the carbon atoms to which they are attached, form an aryl ring having 6 to 10 ring carbon atoms. In some embodiments, two adjacent $R^1$ groups, together with the carbon atoms to which they are attached, form an aryl ring having 6 ring carbon atoms.
In some embodiments, $R^2$ is methyl.
In some embodiments, $R^3$ is ethyl.
In some embodiments, $R^2$ is methyl and $R^3$ is ethyl.
In some embodiments, the compound of Formula Ia is a compound of Formula II:

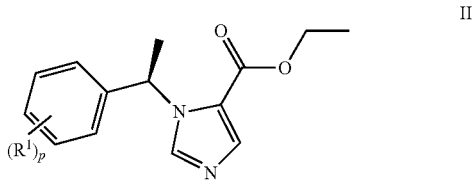

or a pharmaceutically acceptable salt thereof.
In some embodiments, the compound of Formula Ia is a compound of Formula III:

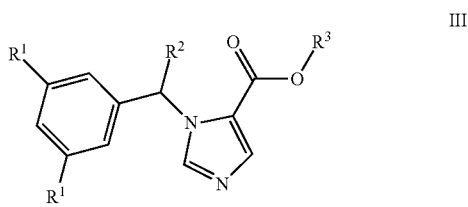

or a pharmaceutically acceptable salt thereof.

In some embodiments, the compound of Formula Ia is a compound of Formula IV:

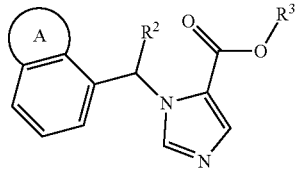

IV or a pharmaceutically acceptable salt thereof, wherein ring A is an aryl ring having 6 to 10 ring carbon atoms.

In some embodiments, the compound of Formula Ia is a compound of Formula V:

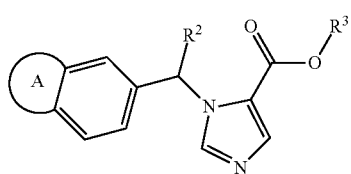

V or a pharmaceutically acceptable salt thereof, wherein ring A is an aryl ring having 6 to 10 ring carbon atoms.

In some embodiments, the compound of Formula Ia is a compound of Formula VI:

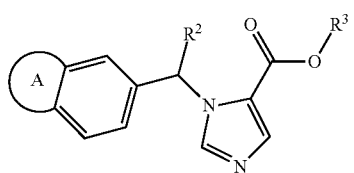

VI or a pharmaceutically acceptable salt thereof, wherein ring A is an aryl ring having 6 to 10 ring carbon atoms.

In some embodiments, the compound of Formula Ia is selected from the group consisting of:

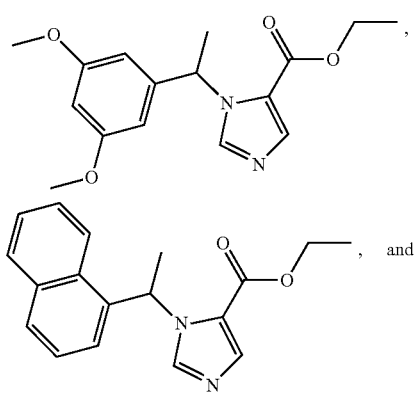

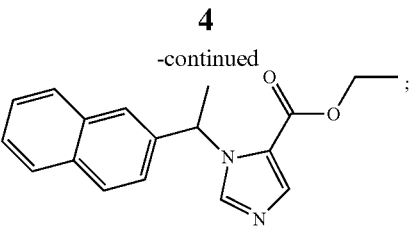

or a pharmaceutically acceptable salt thereof.

In some embodiments, the compound of Formula Ia is selected from the group consisting of:

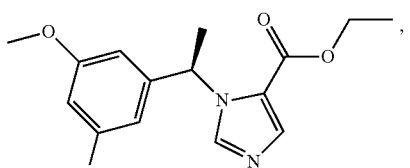

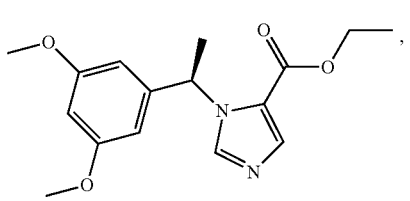 [SMILES: CCOC(=O)c1cncn1[C@H](C)c1cc(OC)cc(OC)c1]

or a pharmaceutically acceptable salt thereof.

In some embodiments, the compound of Formula Ia is:

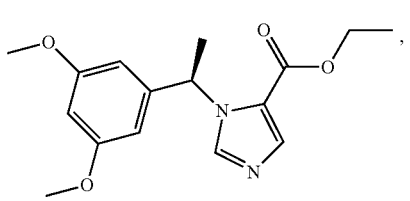 [SMILES: CCOC(=O)c1cncn1[C@H](C)c1cc(OC)cc(OC)c1]

or a pharmaceutically acceptable salt thereof.

The present application further provides a pharmaceutical composition, comprising a compound provided herein (e.g., a compound of any of Formulas I-VIb), or a pharmaceutically acceptable salt thereof, and at least one pharmaceutically acceptable carrier.

The present application further provides a method of inhibiting steroidogenesis in a cell or tissue, comprising contacting the cell or tissue with a compound provided herein (e.g., a compound of any of Formulas I-VIb), or a pharmaceutically acceptable salt thereof.

The present application further provides a method of inhibiting steroidogenesis (e.g., inhibiting adrenocortical steroid synthesis) in a subject, comprising administering to the subject a therapeutically effective amount of a compound provided herein (e.g., a compound of any of Formulas I-VIb), or a pharmaceutically acceptable salt thereof.

The present application further provides a method of inhibiting 11β-hydroxylase activity in a cell or tissue, comprising contacting the cell or tissue with a compound provided herein (e.g., a compound of any of Formulas I-VIb), or a pharmaceutically acceptable salt thereof.

The present application further provides a method of inhibiting 11β-hydroxylase activity in a subject, comprising administering to the subject a therapeutically effective amount of a compound provided herein (e.g., a compound of any of Formulas I-VIb), or a pharmaceutically acceptable salt thereof.

The present application further provides a method of treating a disease associated with abnormal steroidogenesis in a subject, comprising administering to the subject a compound provided herein (e.g., a compound of any of Formulas I-VIb), or a pharmaceutically acceptable salt thereof.

In some embodiments, the disease is selected from the group consisting of Cushing's syndrome, hypercortisolemia, hypertension, diabetes, immunosuppression, water retention, depression, poor wound healing, fatigue, or any combination thereof. In some embodiments, the disease is Cushing's syndrome.

In some embodiments, the therapeutically effective amount is an amount such that the subject does not exhibit a loss of righting reflex. In some embodiments, the therapeutically effective amount is an amount such that the subject does not exhibit loss of consciousness. In some embodiments, the therapeutically effective amount is an amount such that the subject does not exhibit loss of consciousness associated with enhanced receptor function of the $GABA_A$ receptor.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 2C shows etomidate and dimethoxy-etomidate concentration-response curves for potentiation of $EC_5$ GABA evoked currents. Each symbol is the mean±SEM derived from 4 different oocytes. The curves are fits of the datasets to a three parameter Hill equation with the minimum constrained to 5%. For etomidate, the fit yielded a half-maximal potentiating concentration of 1.1 μM (95% CI 1.1 to 1.9 μM) and a maximum peak current amplitude at high etomidate concentrations of 103% (95% CI, 99 to 109%) of that produced by 1 mM GABA. For dimethoxy-etomidate, the fit yielded a half-maximal potentiating concentration of 210 μM (95% CI, 51 to 830 μM) and a maximum peak current value at high concentrations of 11% (95% CI, 8 to 143%).

DETAILED DESCRIPTION

Figures 1A, 1B, 1C:
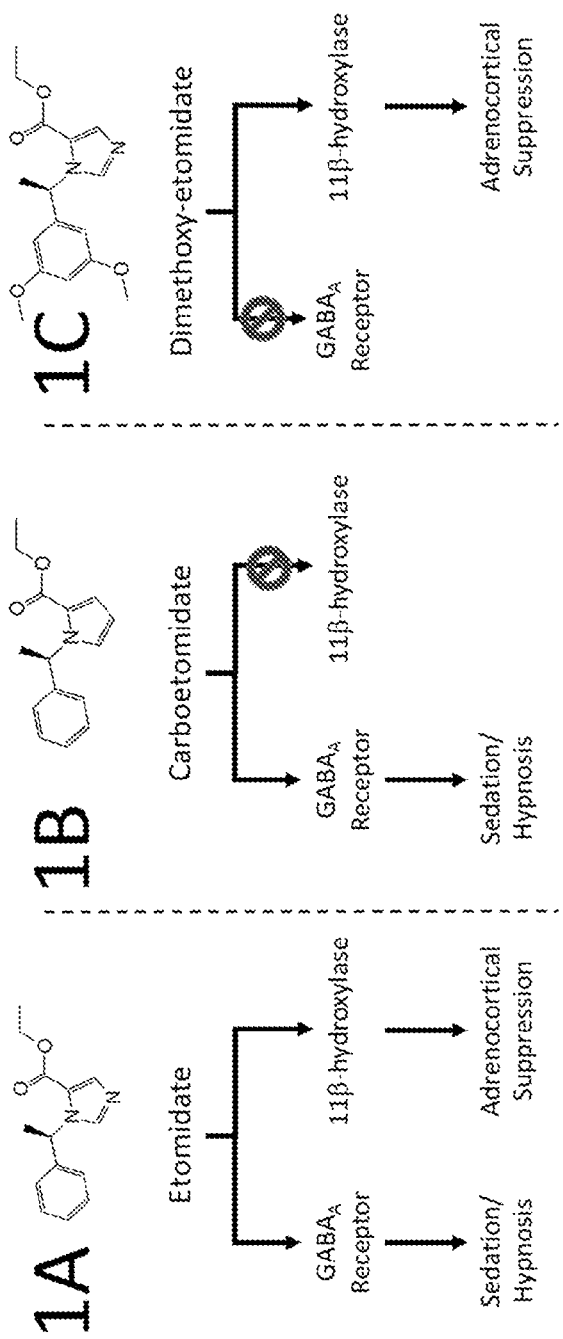
FIGS. 1A-1C show the chemical structures of ethyl (R)-1-(1-phenylethyl)-1H-imidazole-5-carboxylate (i.e., etomidate) (FIG. 1A), ethyl (R)-1-(1-phenylethyl)-1H-pyrrole-2-carboxylate (i.e., carboetomidate) (FIG. 1B), and ethyl (R)-1-(1-(3,5-dimethoxyphenyl)ethyl)-1H-imidazole-5-carboxylate (i.e., dimethoxy-etomidate) (FIG. 1C) along with the major targets of each compound. Etomidate has two major targets: the GABAA receptor and 11β-hydroxylase, which are responsible for etomidate's sedative-hypnotic and steroidogenesis inhibitory activities, respectively (FIG. 1A). Carboetomidate shows activity towards $GABA_A$ receptor and minimal activity towards 11β-hydroxylase (FIG. 2B), and dimethoxy-etomidate shows activity towards 11β-hydroxylase and minimal activity towards $GABA_A$ receptor (FIG. 1C).

Ethyl (R)-1-(1-phenylethyl)-1H-imidazole-5-carboxylate (i.e., etomidate) produces sedation/hypnosis and inhibits cortisol synthesis by binding to distinct protein targets (FIG. 1A). The former activity results from etomidate binding to the $GABA_A$ receptor, producing enhanced receptor function (see e.g., Belelli et al., *Neuropharmacology*, 2003, 45:57-71; Jurd et al., *Faseb. J.*, 2003, 17:250-252; Franks, *Br. J. Pharmacol.*, 2006, 147 Suppl 1:S72-81; Forman, *Anesthesiology*, 2011, 114:695-707). The latter activity results primarily from etomidate binding to the active site of the adrenocortical enzyme 11β-hydroxylase, producing inhibition of enzymatic activity (see e.g., de Jong et al., *J. Clin. Endocrinol. Metab.*, 1984, 59:1143-1147; Fry and Griffiths, *Clin. Endocrinol. (Oxf)*, 1984, 20:625-629; Allolio et al., *Clin. Endocrinol. (Oxf).*, 1985, 22:281-286).

Although there are currently no United States Food and Drug Administration (FDA) approved steroidogenesis inhibitors, ketoconazole, metyrapone, mitotane, and etomidate are clinically approved for other uses and used off-label to treat patients with Cushing's Syndrome (see e.g., Daniel and Newell-Price, *Eur. J. Endocrinol.*, 2015, 172:R263-280; Ambrogio and Cavagnini, *J. Endocrinol. Invest.*, 2016, 39:957-965). Steroidogenesis inhibitors vary in the mechanisms by which they produce their therapeutic effects and commonly produce adverse effects that limit their dosing and efficacy (Daniel and Newell-Price, *Eur. J. Endocrinol.*, 2015, 172:R263-280). Consequently, long-term control of hypercortisolemia is not achieved in 30% of patients with Cushing's Disease even when pharmacotherapy is combined with pituitary resection(s), radiation, and bilateral adrenalectomy (Geer et al., *Endocr. Pract.*, 2017, 23:962-970). Unfortunately, the adverse effects and treatment failures with these drugs are common and only etomidate—which is the most potent of the inhibitors—is completely efficacious (see e.g., Lambert et al., *Ann. Clin. Biochem.*, 1986, 23 (Pt 3):225-229; Lamberts et al., *J. Pharmacol. Exp. Ther.*, 1987, 240:259-264; Preda et al., *Eur. J. Endocrinol.*, 2012, 167:137-143; Cuevas-Ramos and Fleseriu, *J. Endocrinol.*, 2014, 223:R19-39; Gadelha and Vieira Neto, *Clin. Endocrinol. (Oxf).* 2014, 80:1-12; Ambrogio and Cavagnini, *J. Endocrinol. Invest.*, 2016, 39:957-965). However, such efficacy is achieved with etomidate only by using doses that risk producing sedation or hypnosis (i.e., unconsciousness) (see e.g., Engelhardt and Weber, *J. Steroid Biochem. Mol. Biol.*, 1994, 49:261-267; Preda et al., *Eur. J. Endocrinol.*, 2012, 167:137-143; Cuevas-Ramos and Fleseriu, *J. Endocrinol.*, 2014, 223:R19-39; Tritos and Biller, *J. Neurooncol.*, 2014, 117:407-414; Daniel and Newell-Price, *Eur. J. Endocrinol.*, 2015, 172:R263-280).

Previously reported work has demonstrated that by changing a single atom in etomidate's molecular structure to form carboetomidate, the binding affinity to 11β-hydroxylase and adrenocortical inhibitory potency was reduced by three-orders of magnitude while retaining potent $GABA_A$ receptor positive modulatory activity and sedative-hypnotic action (FIG. 1B) (see e.g., Cotten et al., *Anesthesiology*, 2010, 111:240-249; Shanmugasundararaj et al., *Anesth. Analg.*, 2013, 116:1249-1256; Pejo et al., *Anesthesiology*, 2016, 125:943-951). In contrast, the present application provides etomidate analogs that possess the reverse pharmacology of carboetomidate on these two targets (FIG. 1C), i.e., the compounds provided herein retain etomidate's exceptionally high potency as an inhibitor of steroid synthesis but lack its sedative-hypnotic activity. As such, the compounds provided herein may be useful for treating disorders associated with abnormal steroidogenesis, such as Cushing's Syndrome.

Compounds

The present application provides a compound of Formula I:

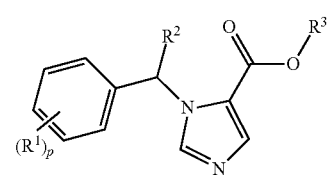

or a pharmaceutically acceptable salt thereof, wherein:
each $R^1$ is independently selected from the group consisting of halo and $C_{1-6}$ alkoxy;
or, alternatively, two adjacent $R^1$ groups, together with the carbon atoms to which they are attached, form an aryl ring having 6 to 10 ring carbon atoms;
$R^2$ is $C_{1-4}$ alkyl;
$R^3$ is $C_{1-4}$ alkyl; and
p is 1, 2, or 3.

In some embodiments, p is 1 or 2. In some embodiments, p is 2 or 3. In some embodiments, p is 1. In some embodiments, p is 2. In some embodiments, p is 3.

In some embodiments, each $R^1$ is independently selected from the group consisting of halo and $C_{1-4}$ alkoxy. In some embodiments, each $R^1$ is an independently selected halo group. In some embodiments, each $R^1$ is an independently selected $C_{1-4}$ alkoxy group. In some embodiments, each $R^1$ is independently selected from the group consisting of fluoro and methoxy. In some embodiments, each $R^1$ is fluoro. In some embodiments, each $R^1$ is independently selected from the group consisting of chloro, bromo, and iodo. In some embodiments, each $R^1$ is independently selected from the group consisting of fluoro, chloro, bromo, iodo, and methoxy. In some embodiments, each $R^1$ is methoxy.

In some embodiments, each $R^1$ is independently selected from the group consisting of halo and $C_{1-4}$ alkoxy, and p is 1 or 2. In some embodiments, each $R^1$ is independently selected from the group consisting of halo and $C_{1-4}$ alkoxy, and p is 1. In some embodiments, each $R^1$ is independently selected from the group consisting of halo and $C_{1-4}$ alkoxy, and p is 2.

In some embodiments, each $R^1$ is an independently selected halo group and p is 1 or 2. In some embodiments, $R^1$ is halo and p is 1. In some embodiments, each $R^1$ is an independently selected halo group and p is 2. In some embodiments, $R^1$ is fluoro and p is 1. In some embodiments, $R^1$ is selected from the group consisting of chloro, bromo, and iodo, and p is 1. In some embodiments, each $R^1$ is independently selected from the group consisting of chloro, bromo, and iodo, and p is 2. In some embodiments, each $R^1$ is independently selected from the group consisting of fluoro, chloro, bromo, iodo, and methoxy, and p is 2. In some embodiments, each $R^1$ is methoxy, and p is 2.

In some embodiments, two adjacent $R^1$ groups, together with the carbon atoms to which they are attached, form an aryl ring having 6 to 10 ring carbon atoms. In some embodiments, two adjacent $R^1$ groups, together with the carbon atoms to which they are attached, form an aryl ring having 6 ring carbon atoms.

In some embodiments, two adjacent R¹ groups, together with the carbon atoms to which they are attached, form an aryl ring A selected from:

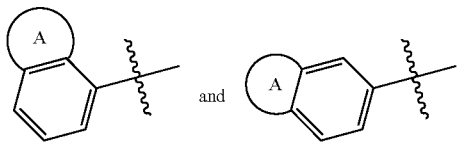

and wherein:

∿∿∿ indicates the bond between the fused phenyl group and —CH(R²)— group of Formula I; and ring A comprises 6 to 10 carbon atoms.

In some embodiments, two adjacent R¹ groups, together with the carbon atoms to which they are attached, form an aryl ring A selected from:

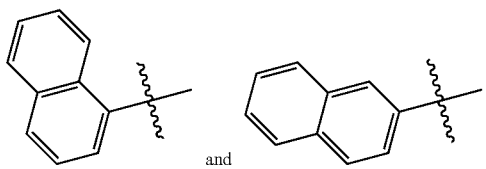 [SMILES: *c1cccc2ccccc12 ; *c1ccc2ccccc2c1]

and wherein ∿∿∿ indicates the bond between the fused phenyl group and —CH(R²)— group of Formula I.

In some embodiments, R² is methyl.
In some embodiments, R³ is ethyl.
In some embodiments, R² is methyl and R³ is ethyl.
In some embodiments, the compound of Formula I is a compound of Formula Ia:

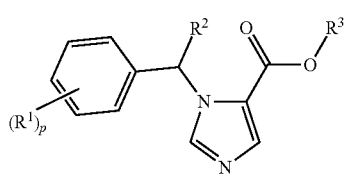

Ia or a pharmaceutically acceptable salt thereof, wherein:
each R¹ is an independently selected $C_{1-6}$ alkoxy;
or, alternatively, two adjacent R¹ groups, together with the carbon atoms to which they are attached, form an aryl ring having 6 to 10 ring carbon atoms;
R² is $C_{1-4}$ alkyl;
R³ is $C_{1-4}$ alkyl; and
p is 2 or 3.

In some embodiments of the compound of Formula Ia, p is 2. In some embodiments, p is 3.

In some embodiments of the compound of Formula Ia, each R¹ is methoxy. In some embodiments of the compound of Formula Ia, each R¹ is an independently selected $C_{1-4}$ alkoxy group, and p is 2. In some embodiments of the compound of Formula Ia, each R¹ is an independently selected $C_{1-4}$ alkoxy group, and p is 3. In some embodiments of the compound of Formula Ia, each R¹ is methoxy, and p is 2.

In some embodiments of the compound of Formula Ia, two adjacent R¹ groups, together with the carbon atoms to which they are attached, form an aryl ring having 6 to 10 ring carbon atoms. In some embodiments of the compound of Formula Ia, two adjacent R¹ groups, together with the carbon atoms to which they are attached, form an aryl ring having 6 ring carbon atoms.

In some embodiments of the compound of Formula Ia, two adjacent R¹ groups, together with the carbon atoms to which they are attached, form an aryl ring A selected from:

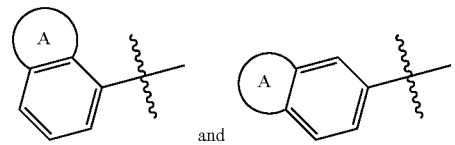

and wherein:

∿∿∿ indicates the bond between the fused phenyl group and —CH(R²)— group of Formula I; and ring A comprises 6 to 10 carbon atoms.

In some embodiments of the compound of Formula Ia, two adjacent R¹ groups, together with the carbon atoms to which they are attached, form an aryl ring A selected

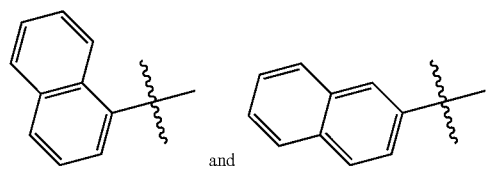 [SMILES: *c1cccc2ccccc12 ; *c1ccc2ccccc2c1]

and wherein ∿∿∿ indicates the bond between the fused phenyl group and —CH(R²)— group of Formula Ia.

In some embodiments of the compound of Formula Ia, R² is methyl.

In some embodiments of the compound of Formula Ia, R³ is ethyl.

In some embodiments of the compound of Formula Ia, R² is methyl and R³ is ethyl.

In some embodiments, the compound of Formula I is a compound of Formula Ib:

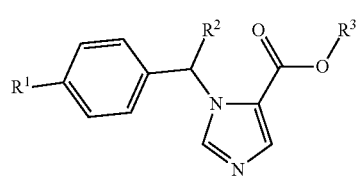

Ib or a pharmaceutically acceptable salt thereof, wherein variables R¹, R², and R³ are defined according to the definitions provided herein for compounds of Formula I.

In some embodiments, the compound of Formula I is a compound of Formula Ic:

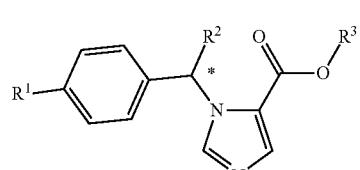

Ic or a pharmaceutically acceptable salt thereof, wherein variables R¹, R², and R³ are defined according to the definitions provided herein for compounds of Formula I, and wherein the starred carbon (*) is in the (R)-configuration.

In some embodiments, the compound of Formula I is a compound of Formula Id:

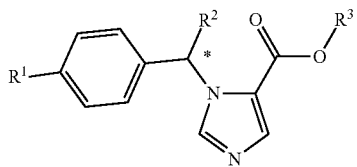

Id or a pharmaceutically acceptable salt thereof, wherein variables $R^1$, $R^2$, and $R^3$ are defined according to the definitions provided herein for compounds of Formula I, and wherein the starred carbon (*) is in the (S)-configuration.

In some embodiments, the compound of Formula I or Formula Ia is a compound of Formula II:

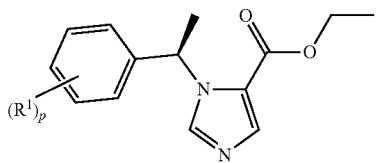

II or a pharmaceutically acceptable salt thereof, wherein variables $R^1$ and p are defined according to the definitions provided herein for compounds of Formula I or Formula Ia.

In some embodiments, the compound of Formula I or Formula Ia is a compound of Formula III:

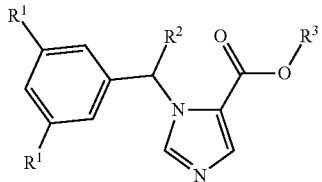

III or a pharmaceutically acceptable salt thereof, wherein variables wherein variables $R^1$, $R^2$, and $R^3$ are defined according to the definitions provided herein for compounds of Formula I or Formula Ia.

In some embodiments, the compound of Formula I or Formula Ia is a compound of Formula IIIa:

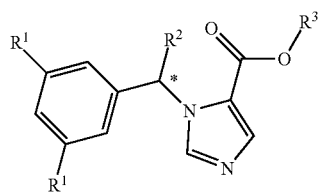

IIIa or a pharmaceutically acceptable salt thereof, wherein variables wherein variables $R^1$, $R^2$, and $R^3$ are defined according to the definitions provided herein for compounds of Formula I or Formula Ia, and wherein the starred carbon (*) is in the (R)-configuration.

In some embodiments, the compound of Formula I or Formula Ia is a compound

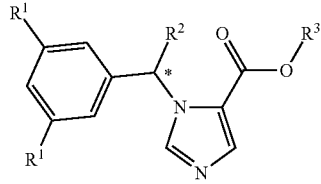

IIIb or a pharmaceutically acceptable salt thereof, wherein variables wherein variables $R^1$, $R^2$, and $R^3$ are defined according to the definitions provided herein for compounds of Formula I or Formula Ia, and wherein the starred carbon (*) is in the (S)-configuration.

In some embodiments, the compound of Formula I or Formula Ia is a compound of Formula IV:

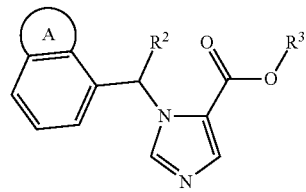

IV or a pharmaceutically acceptable salt thereof, wherein ring A is an aryl ring having 6 to 10 ring carbon atoms, and variables $R^2$, and $R^3$ are defined according to the definitions provided herein for compounds of Formula I or Formula Ia.

In some embodiments, the compound of Formula I or Formula Ia is a compound of Formula IVa:

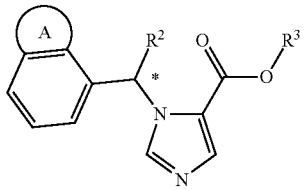

IVa or a pharmaceutically acceptable salt thereof, wherein ring A is an aryl ring having 6 to 10 ring carbon atom, variables $R^2$ and $R^3$ are defined according to the definitions provided herein for compounds of Formula I or Formula Ia, and wherein the starred carbon (*) is in the (R)-configuration.

In some embodiments, the compound of Formula I or Formula Ia is a compound of Formula IVb:

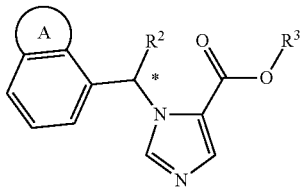

IVb or a pharmaceutically acceptable salt thereof, wherein ring A is an aryl ring having 6 to 10 ring carbon atom, variables $R^2$ and $R^3$ are defined according to the definitions provided herein for compounds of Formula I or Formula Ia, and wherein the starred carbon (*) is in the (S)-configuration.

In some embodiments, the compound of Formula I or Formula Ia is a compound of Formula V:

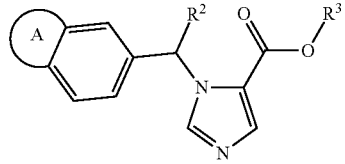

V or a pharmaceutically acceptable salt thereof, wherein ring A is an aryl ring having 6 to 10 ring carbon atoms, and variables $R^2$ and $R^3$ are defined according to the definitions provided herein for compounds of Formula I or Formula Ia.

In some embodiments, the compound of Formula I or Formula Ia is a compound of Formula Va:

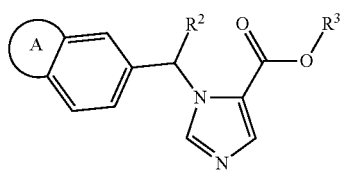

Va or a pharmaceutically acceptable salt thereof, wherein ring A is an aryl ring having 6 to 10 ring carbon atoms, and variables $R^2$ and $R^3$ are defined according to the definitions provided herein for compounds of Formula I or Formula Ia, and wherein the starred carbon (*) is in the (R)-configuration.

In some embodiments, the compound of Formula I or Formula Ia is a compound of Formula Vb:

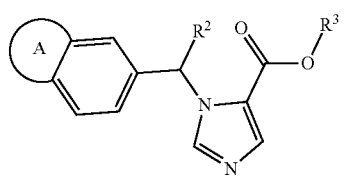

Vb or a pharmaceutically acceptable salt thereof, wherein ring A is an aryl ring having 6 to 10 ring carbon atoms, and variables $R^2$ and $R^3$ are defined according to the definitions provided herein for compounds of Formula I or Formula Ia, and wherein the starred carbon (*) is in the (S)-configuration.

In some embodiments, the compound of Formula I or Formula Ia is a compound of Formula VI:

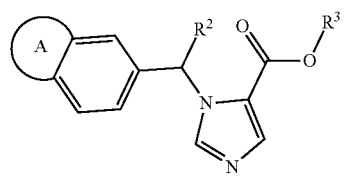

VI or a pharmaceutically acceptable salt thereof, wherein ring A is an aryl ring having 6 to 10 ring carbon atoms, and variables $R^2$ and $R^3$ are defined according to the definitions provided herein for compounds of Formula I or Formula Ia.

In some embodiments, the compound of Formula I or Formula Ia is a compound of Formula VIa:

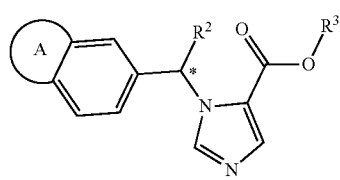

VIa or a pharmaceutically acceptable salt thereof, wherein ring A is an aryl ring having 6 to 10 ring carbon atoms, and variables $R^2$ and $R^3$ are defined according to the definitions provided herein for compounds of Formula I or Formula Ia, and wherein the starred carbon (*) is in the (R)-configuration.

In some embodiments, the compound of Formula I or Formula Ia is a compound of Formula VIb:

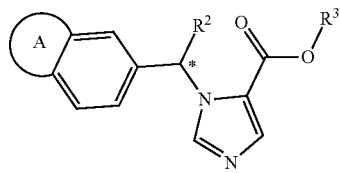

VIb or a pharmaceutically acceptable salt thereof, wherein ring A is an aryl ring having 6 to 10 ring carbon atoms, and variables $R^2$ and $R^3$ are defined according to the definitions provided herein for compounds of Formula I or Formula Ia, and wherein the starred carbon (*) is in the (S)-configuration.

In some embodiments, the compound of Formula I is selected from the group consisting of:

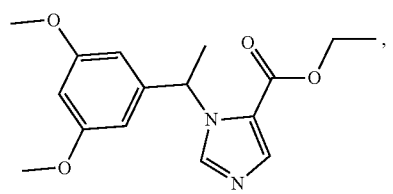

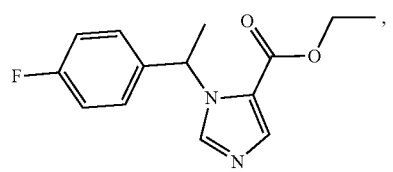

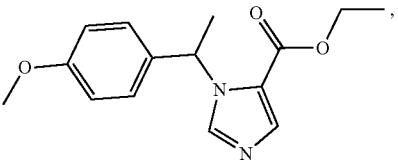

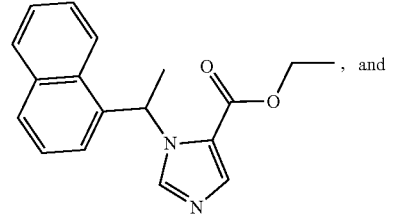

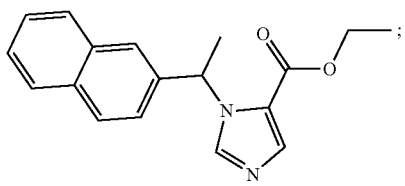

or a pharmaceutically acceptable salt thereof.

In some embodiments, the compound of Formula I is selected from the group consisting of:

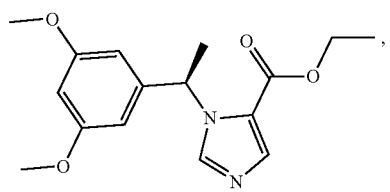

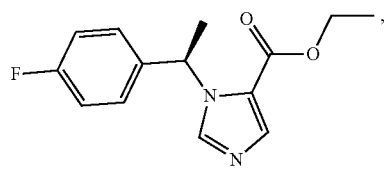

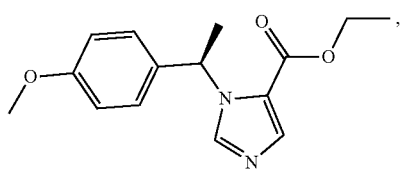

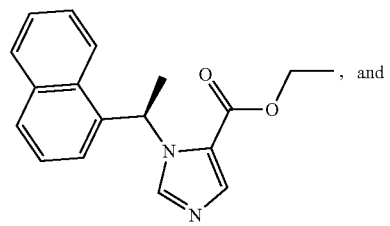

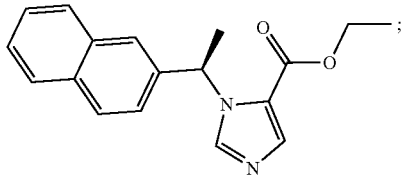

or a pharmaceutically acceptable salt thereof.

In some embodiments, the compound of Formula I or Formula Ia is selected from the group consisting of:

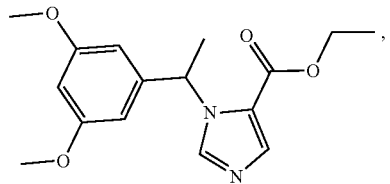

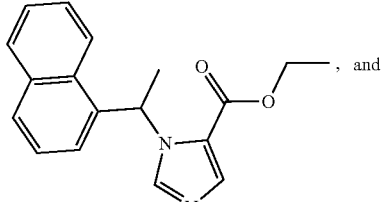

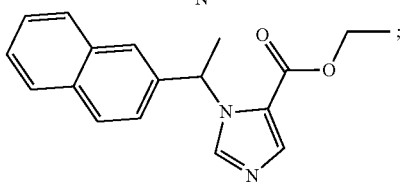

or a pharmaceutically acceptable salt thereof.

In some embodiments, the compound of Formula I is selected from the group consisting of:

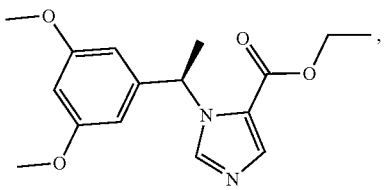

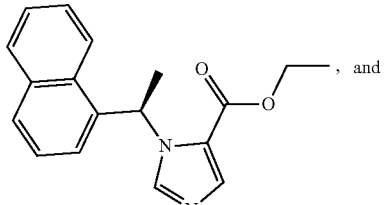

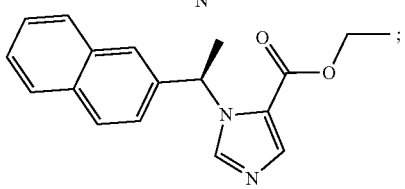

or a pharmaceutically acceptable salt thereof.

In some embodiments, the compound of Formula I or Formula Ia is:

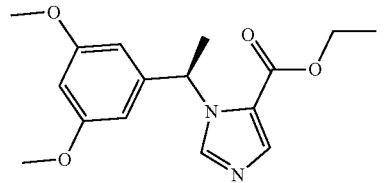 [SMILES: CCOC(=O)c1cncn1[C@H](C)c1cc(OC)cc(OC)c1]

or a pharmaceutically acceptable salt thereof.

Unless specifically defined, compounds and salts provided herein can also include all isotopes of atoms occurring in the intermediates or final compounds. Isotopes include those atoms having the same atomic number but different mass numbers (e.g. $^2$H, $^3$H, $^{13}$C, and the like).

Synthesis

The compounds provided herein (e.g., compounds of any of Formulas I-VIb), or pharmaceutically acceptable salts thereof, can be prepared according to the procedures described in Scheme 1.

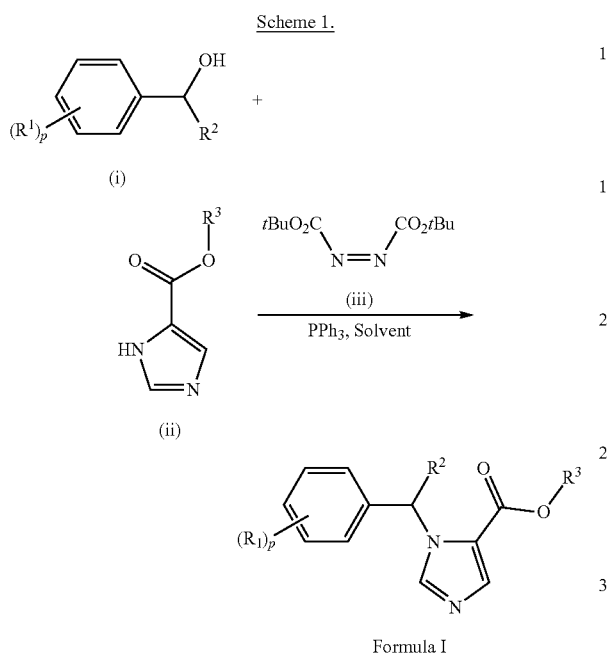

Formula I

For example, hydroxy-compound (i) can be coupled with the heteroaryl compound (ii) in the presence of diazene compound (iii) and triphenyl phosphine in a solvent (e.g., tetrahydrofuran) to form the compound of Formula I.

The compounds provided herein, or pharmaceutically acceptable salts thereof, can also be prepared, for example, according to the procedure shown below in Scheme 2.

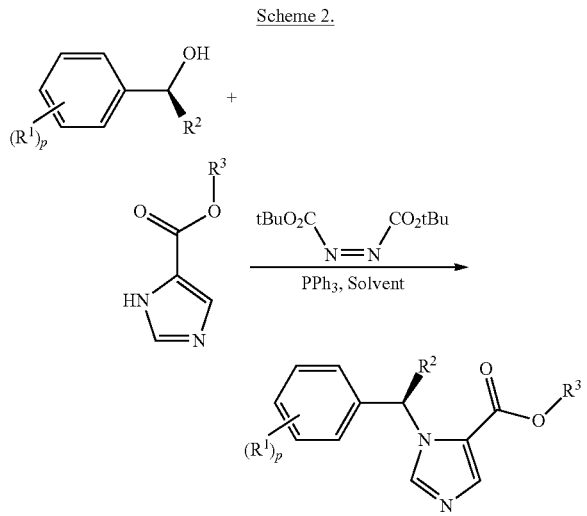

An exemplary scheme for preparing a compound of Formula I (Example 1) is shown below in Scheme 3.

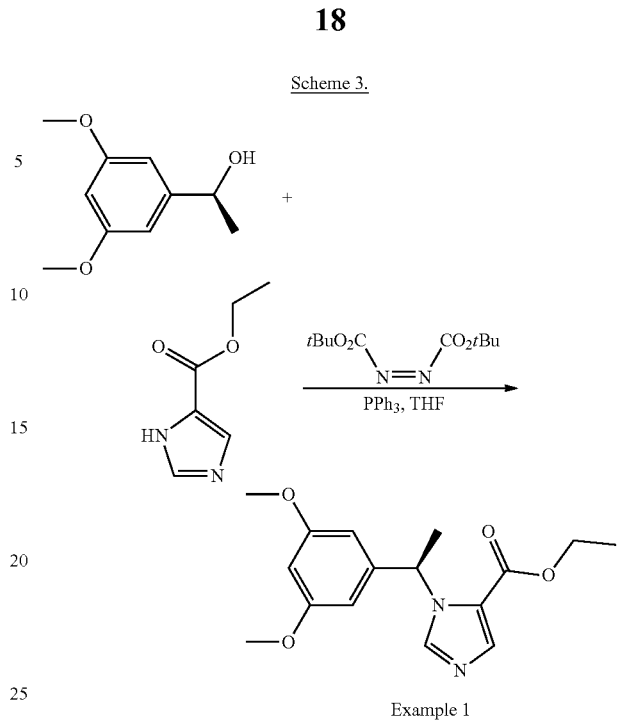

Example 1

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$-includes both —NR(CR'R")$_n$— and —(CR'R")$_n$NR—. Where the structure clearly requires a linking group, the Markush variables listed for that group are understood to be linking groups.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 4 carbon atoms, from 1 to 3 carbon atoms, or 1 to 2 carbon atoms.

As used herein, the term "halo" refers to F, Cl, Br, or I. In some embodiments, the halo is F, Cl, or Br. In some embodiments, the halo is F.

As used herein, the term "$C_{n-m}$ alkoxy" refers to a group of formula —O-alkyl, wherein the alkyl group has n to m carbons. Exemplary alkoxy groups include, but are not limited to, methoxy, ethoxy, and propoxy (e.g., n-propoxy and isopropoxy). In some embodiments, the alkoxy group has from 1 to 6 carbon atoms, from 1 to 4 carbon atoms, or from 1 to 2 carbon atoms.

As used herein, the term "aryl" refers to a monocyclic or polycyclic (e.g., having 2, 3 or 4 fused rings) aromatic hydrocarbon including, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and Journal of Pharmaceutical Science, 66, 2 (1977). Conventional methods for preparing salt forms are described, for example, in *Handbook of Pharmaceutical Salts: Properties, Selection, and Use*, Wiley-VCH, 2002.

Methods of Use

The present application further provides a method of inhibiting steroidogenesis (e.g., reducing steroiogenesis). In some embodiments, the method comprises inhibiting steroidogenesis (e.g., inhibiting adrenocortical steroid synthesis) in a cell or tissue, comprising contacting the cell or tissue with a compound provided herein (e.g., a compound of any of Formulas I-VIb), or a pharmaceutically acceptable salt thereof. In some embodiments, the method is an in vitro method. In some embodiments, the method is an in vivo method.

The present application further provides a method of inhibiting steroidogenesis (e.g., inhibiting adrenocortical steroid synthesis) in a subject. In some embodiments, the method comprises administering to the subject a compound provided herein (e.g., a compound of any of Formulas I-VIb), or a pharmaceutically acceptable salt thereof. In some embodiments, the method comprises administering to the subject a therapeutically effective amount of a compound provided herein (e.g., a compound of any of Formulas I-VIb), or a pharmaceutically acceptable salt thereof.

The present application further provides a method of inhibiting 11β-hydroxylase activity in a cell or tissue, comprising contacting the cell or tissue with a compound provided herein (e.g., a compound of any of Formulas I-VIb), or a pharmaceutically acceptable salt thereof. In some embodiments, the method is an in vitro method. In some embodiments, the method is an in vivo method.

The present application further provides a method of inhibiting 11β-hydroxylase activity in a subject. In some embodiments, the method comprises administering to the subject a compound provided herein (e.g., a compound of any of Formulas I-VIb), or a pharmaceutically acceptable salt thereof. In some embodiments, the method comprises administering to the subject a therapeutically effective amount of compound provided herein (e.g., a compound of any of Formulas I-VIb), or a pharmaceutically acceptable salt thereof.

The present application further provides a method of treating a disease associated with abnormal steroidogenesis in a subject. In some embodiments, the abnormal steroidogenesis comprises overproduction of steroids in the subject, compared to a normal or healthy subject. In some embodiments, the abnormal steroidogenesis comprises overproduction of adrenocortical steroids in the subject, compared to a normal or healthy subject.

In some embodiments, the method comprises administering to the subject a compound provided herein (e.g., a compound of any of Formulas I-VIb), or a pharmaceutically acceptable salt thereof. In some embodiments, the method comprises administering to the subject a therapeutically effective amount of a compound provided herein (e.g., a compound of any of Formulas I-VIb), or a pharmaceutically acceptable salt thereof.

In some embodiments, the disease is associated with abnormal adrenocortical steroidogenesis. In some embodiments, the disease is selected from the group consisting of Cushing's syndrome, hypercortisolemia, hypertension, diabetes, immunosuppression, water retention, depression, poor wound healing (e.g., slow wound healing), and fatigue, or any combination thereof. In some embodiments, the disease is selected from the group consisting of Cushing's syndrome and hypercortisolemia, or a combination thereof. In some embodiments, the disease is Cushing's syndrome.

As used here, the term "subject," refers to any animal, including mammals. Example subjects include, but are not limited to, mice, rats, rabbits, dogs, cats, swine, cattle, sheep, horses, primates, and humans. In some embodiments, the subject is a human.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is from about 1 mg/kg to about 100 mg/kg, for example, about 1 mg/kg to about 75 mg/kg, about 1 mg/kg to about 50 mg/kg, about 1 mg/kg to about 25 mg/kg, about 1 mg/kg to about 10 mg/kg, about 10 mg/kg to about 100 mg/kg, about 10 mg/kg to about 75 mg/kg, about 10 mg/kg to about 50 mg/kg, about 10 mg/kg to about 25 mg/kg, about 25 mg/kg to about 100 mg/kg, about 25 mg/kg to about 75 mg/kg, about 25 mg/kg to about 50 mg/kg, about 50 mg/kg to about 100 mg/kg, about 50 mg/kg to about 75 mg/kg, or about 75 mg/kg to about 100 mg/kg.

In some embodiments, the therapeutically effective amount is an amount such that the subject does not exhibit a loss of righting reflex. In some embodiments, the therapeutically effective amount is an amount such that the subject does not exhibit loss of consciousness. In some embodiments, the therapeutically effective amount is an amount such that the subject does not exhibit loss of consciousness associated with enhanced receptor function of the $GABA_A$ receptor.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional therapeutic agents such as, for example, pituitary-targeted agents, glucocorticoid receptor antagonists, and inhibitors of steroidogenesis can be used in combination with the compounds and salts provided herein for use in the methods described herein.

Exemplary pituitary-targeted agents include, but are not limited to, cabergoline, pasireotide, retinoic acid, and EGFR-antagonists.

Exemplary glucocorticoid receptor antagonists include, but are not limited to, mifepristone.

Exemplary inhibitors of steroidogenesis include, but are not limited to, ketoconazole, fluconazole, metyrapone, mitotane, and etomidate.

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Compositions & Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

The invention will be described in greater detail by way of specific examples. The following examples are offered for illustrative purposes, and are not intended to limit the invention in any manner.
General Methods and Materials Dexamethasone was obtained from American Regent (Shirley, N.Y., USA), and ACTH$_{1-24}$ and GABA was from Sigma-Aldrich Chemical Company (St. Louis, Mo.). Etomidate was purchased from Bachem (Torrance, Calif., USA). [$^3$H]-etomidate was prepared from unlabeled etomidate by Perkin-Elmer Life Sciences (Boston, Mass., USA) using a catalytic exchange reaction. The mass fragmentation pattern of [$^3$H]-etomidate showed that all of the tritium was located on the imidazole ring. The specific activity of [$^3$H]-etomidate was 8.6 Ci/mM. Enzyme-linked immunosorbent assay kits for corticosterone were purchased from IDS (Gaithersburg, Md., USA), those for pregnenolone and aldosterone were purchased from Elabscience (Bethesda, Md., USA), and those for progesterone and deoxycorticosterone were purchased from Mybiosource (Cambridge, Mass., USA). Dimethoxy-etomidate were synthesized by Aberjona Laboratories (Beverly, Mass., USA).

Adult male Sprague-Dawley rats (250-350 gm) were purchased from Charles River Laboratories (Wilmington, Mass., USA). *Xenopus laevis* adult female frogs were purchased from Xenopus One (Ann Arbor, Mich., USA).

All individual data points are expressed as the mean±SEM of three to eight independent measurements. Statistical analyses to define a preferred binding model (one site versus two site) for competitive binding studies were carried out using an extra sum-of-squares F test whereas those to assess differences in plasma steroid concentrations were carried out using either a Mann-Whitney U test (for a single comparison) or a Kruskal-Wallis test followed by a Dunn's multiple comparisons test using Prism 6 for Mac OS X. A two-way ANOVA was used to compare the number of myoclonic movements produced by etomidate versus dimethoxy-etomidate during each 5-minute epoch after drug administration. Statistical significance was assumed for p<0.05.

Example 1. Ethyl (R)-1-(1-(3,5-dimethoxyphenyl) ethyl)-1H-imidazole-5-carboxylate (dimethoxy-etomidate)

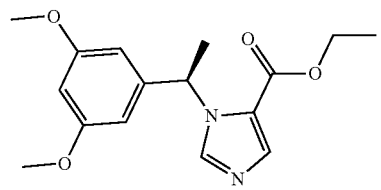 [SMILES: CCOC(=O)c1cncn1[C@H](C)c1cc(OC)cc(OC)c1]

The title compound was prepared according to the procedures described in Schemes 1-3.

Examples 2-5

The compounds of Examples 2-5 were prepared according to the procedures described in Example 1 using appropriately substituted starting materials.

| Ex. No. | Compound Name | Compound Structure |
|---|---|---|
| 2 | ethyl (R)-1-(1-(4-fluorophenyl)ethyl)-1H-imidazole-5-carboxylate | 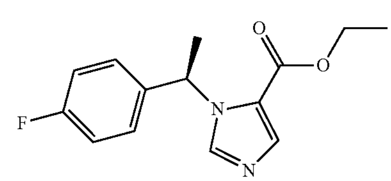 [SMILES: CCOC(=O)c1cncn1[C@H](C)c1ccc(F)cc1] |

-continued

| Ex. No. | Compound Name | Compound Structure |
|---|---|---|
| 3 | ethyl (R)-1-(1-(4-methoxyphenyl)ethyl)-1H-imidazole-5-carboxylate | 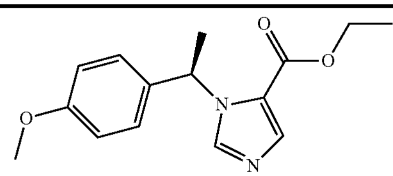 |
| 4 | ethyl (R)-1-(1-(naphthalen-1-yl)ethyl)-1H-imidazole-5-carboxylate | 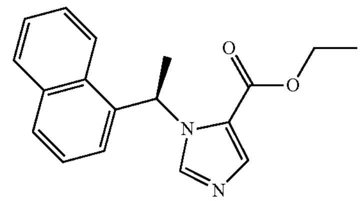 [SMILES: CCOC(=O)c1cncn1[C@H](C)c1cccc2ccccc12] |
| 5 | ethyl (R)-1-(1-(naphthalen-2-yl)ethyl)-1H-imidazole-5-carboxylate | 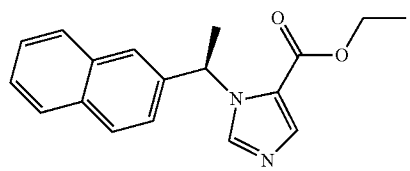 [SMILES: CCOC(=O)c1cncn1[C@H](C)c1ccc2ccccc2c1] |

Example 6. GABA$_A$ Receptor Electrophysiology Studies

Oocytes were harvested from *Xenopus* frogs and injected with messenger RNA encoding the $\alpha_1$, $\beta_3$, and $\gamma_{2L}$ subunits of the human GABA$_A$ receptor (5 ng of messenger RNA total at a subunit ratio of 1:1:3). Oocytes were then incubated in ND96 buffer (96 mM NaCl, 2 mM KCl, 1.8 mM CaCl$_2$, 1 mM MgCl$_2$, 5 mM HEPES, pH=7.4) containing 0.05 mg/mL of gentamicin for 18 to 48 hours at 18° C. before electrophysiological study. Electrophysiological recordings were performed at room temperature using the whole cell two-electrode voltage-clamp technique as previously described (see e.g., Pejo et al, *Anesth. Analg.*, 2012, 115:297-304). For each oocyte, a GABA concentration-peak current response curve was generated to define the GABA concentration that elicits 5% of the current evoked by 1 mM GABA (i.e., EC$_5$ GABA). The effect of drug (etomidate or dimethoxy-etomidate) was then defined in that oocyte by perfusing it with EC$_5$ GABA alone for 15-20 s followed immediately by EC$_5$ GABA+drug at the desired concentration for 20-60 s. The resulting current response was then recorded. The peak current response recorded in the presence of EC$_5$ GABA+drug was then normalized to the peak current response evoked by 1 mM GABA. Between electrophysiological recordings, oocytes were perfused with buffer for at least 3 min to remove GABA (and drug, if present) and to allow receptors to recover from desensitization.

The concentration-response relationships for EC$_5$ GABA potentiation by etomidate and dimethoxy-etomidate were fit to a three parameter Hill equation using Prism 6 for Mac OS X (Graphpad, La Jolla, Calif., USA) to define an EC$_{50}$ and maximal current response in the presence of high drug concentrations (and their respective 95% confidence intervals). In these fits, the minimum was constrained to 5% (by definition, for EC$_5$ evoked currents).

Figures 2A, 2B, 2C:
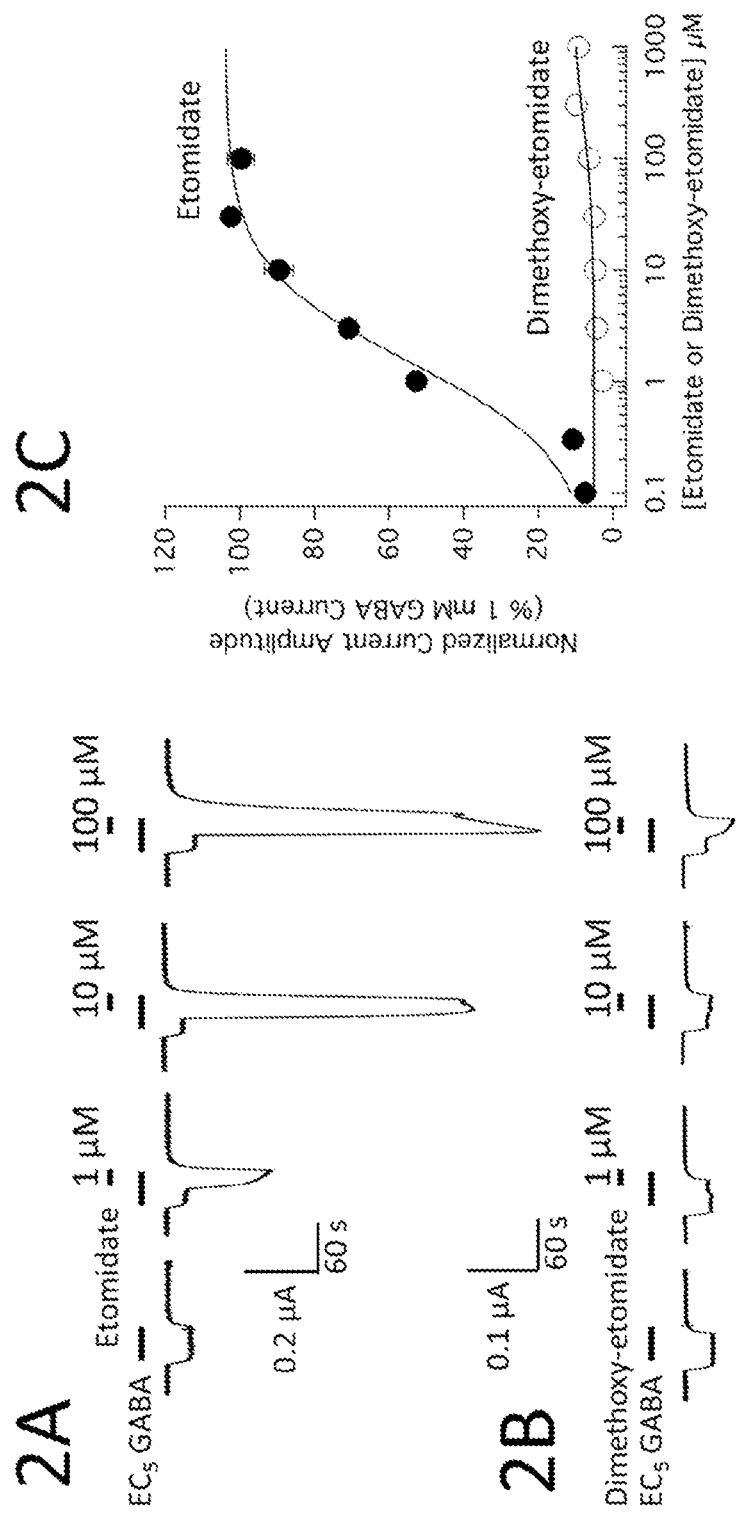
FIGS. 2A-2C show potentiation of $\alpha_1\beta_3\gamma_{2L}$ $GABA_A$ receptor currents by etomidate and dimethoxy-etomidate. Electrophysiological traces showing the potentiating effect of etomidate (FIG. 2A) or dimethoxy-etomidate (FIG. 2B) on currents evoked by a GABA concentration that elicits 5% of the current evoked by 1 mM GABA ($EC_5$ GABA). For each set of traces, currents at all drug concentrations were obtained using the same oocyte.
Figure 9:
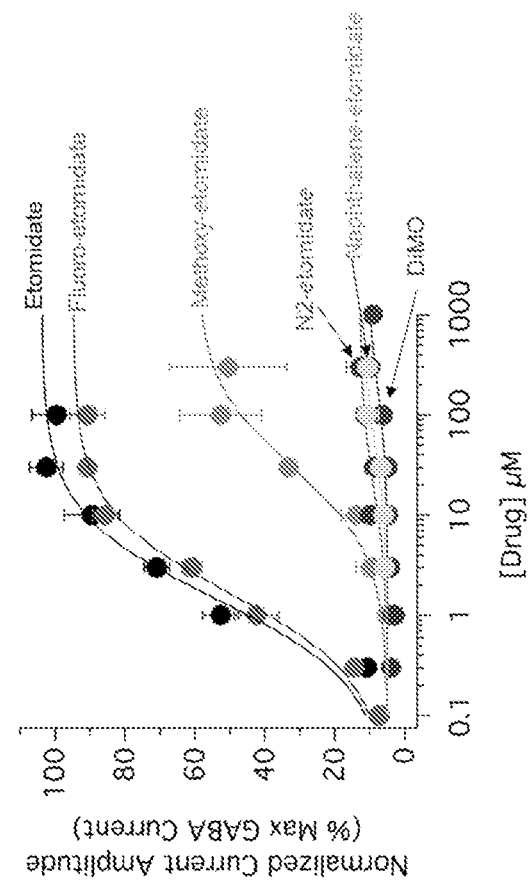
FIG. 9 shows electrophysiological current responses for etomidate and the etomidate analogs of Examples 1-5.
Figure 9:
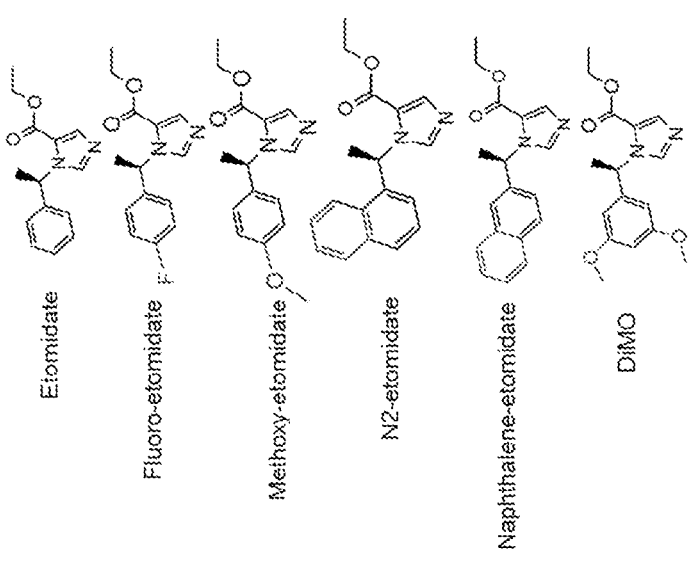

FIGS. 2A-2B show the resulting electrophysiological current responses for etomidate (FIG. 2A) and dimethoxy-etomidate (FIG. 2B). Although peak currents evoked by this low GABA concentration were enhanced by both drugs, the magnitude of enhancement produced by dimethoxy-etomidate was relatively small, ≤⅛$^{th}$ that produced by the same concentration of etomidate. FIG. 2C shows the etomidate and dimethoxy-etomidate concentration-response relationships for this peak current enhancement. Specifically, FIG. 2C shows that etomidate enhanced peak currents in a manner that was concentration-dependent, potent, and highly efficacious. A fit of the etomidate dataset to a Hill equation yielded an EC$_{50}$ of 1.1 µM (95% CI: 1.1-1.9 µM) and a maximum peak current that was 103% (95% CI: 99-109%) of that produced by 1 mM GABA, a maximally activating agonist concentration. Although dimethoxy-etomidate also enhanced peak currents in a concentration-dependent manner, this action was neither potent nor efficacious as fit of the dimethoxy-etomidate dataset to a Hill equation yielded an EC$_{50}$ of 210 µM (95% CI: 51-830 µM) and a maximum peak current that was only 11% (95% CI: 8-14%) of that produced by 1 mM GABA. As shown in FIG. 9, etomidate analogs with larger phenyl ring substituent groups (Examples 4-5) produced electrophysiological current responses similar to dimethoxy-etomidate.

Example 7. Sedative-Hypnotic Activity Studies in Rats

Figures 3A, 3B:
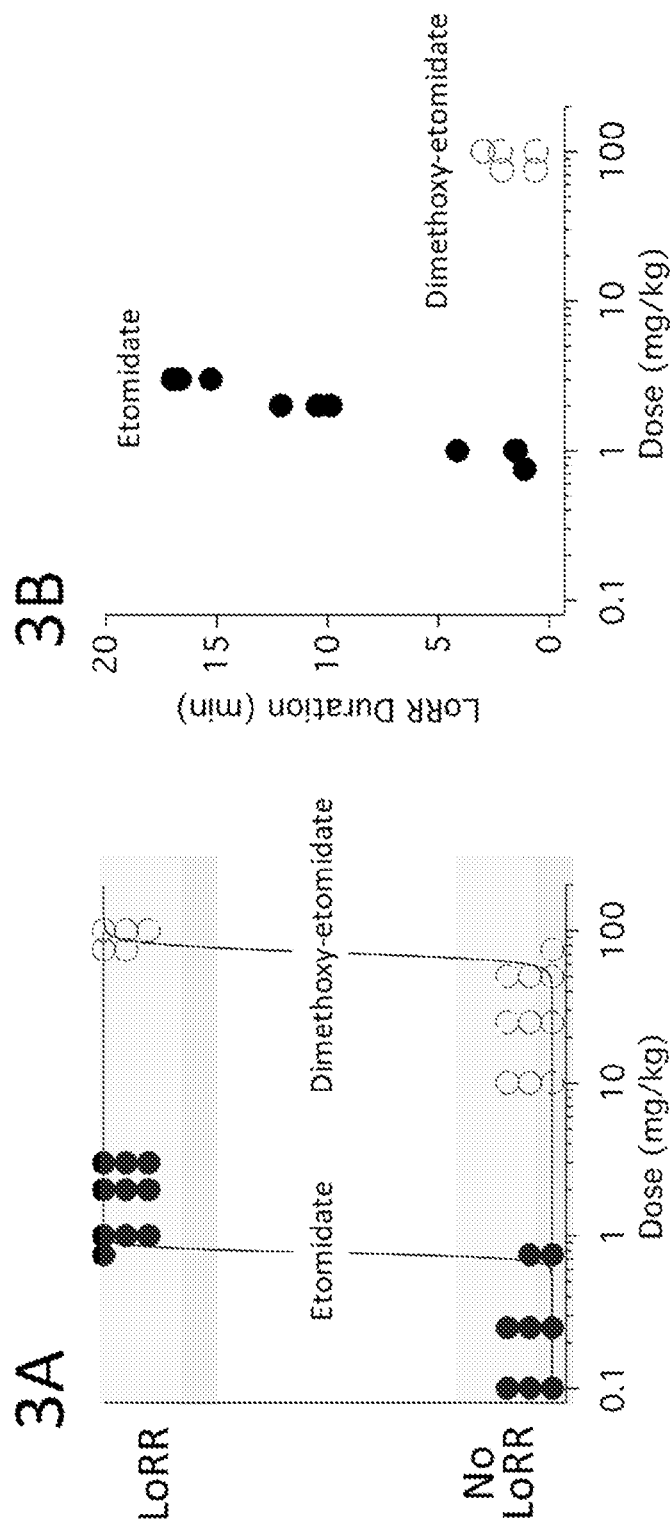
FIG. 3A shows dose-response curves for loss of righting reflexes (LoRR) in rats. A fit of the dose-response relationships yielded $ED_{50}$s of 0.77±0.17 mg/kg for etomidate and 72±13 mg/kg for dimethoxy-etomidate.
FIG. 3B shows dose-response curves for loss of righting reflexes (LoRR) duration in rats. In both panels, each symbol is the result obtained from a single rat experiment.

The sedative-hypnotic potencies of etomidate and dimethoxy-etomidate were assessed in Sprague-Dawley rats using a loss of righting reflexes (LORR) assay (see e.g., Cotten et al, *Anesthesiology*, 2009, 111:240-249). Briefly, the desired dose of drug in dimethyl sulfoxide vehicle (0.1-0.3 mL) was rapidly (<5 s) injected through a 24-gauge intravenous catheter placed in a tail vein. This was followed by a 0.5-mL normal saline flush. Immediately after injection, rats were turned supine. A rat was judged to have LORR if it failed to right (i.e., turn itself back onto all four paws) after drug administration. The duration of LORR was defined as the time from drug injection until the animal spontaneously righted itself onto all four legs. For each drug, the median effective dose ($ED_{50}$) for LORR was determined by fitting the dose-response relationship to a logistic equation using the method of Waud for quantal responses (see e.g., Waud, *J. Pharmacol. Exp. Ther.*, 1972, 183:577-607) with Igor Pro 6.37 (Wavemetrics, Lake Oswego, Oreg., USA), as shown in FIGS. 3A-3B.

Etomidate produced loss of righting reflexes in all rats receiving doses of 1 mg/kg or greater. A fit of the etomidate dose-response relationship for loss of righting reflexes yielded an $ED_{50}$ of 0.77±0.17 mg/kg. In contrast, dimethoxy-etomidate produced loss of righting reflexes in all rats only when administered at a dose of 100 mg/kg, the highest dimethoxy-etomidate dose studied. A fit of the dimethoxy-etomidate dose-response relationship for loss of righting reflexes yielded an $ED_{50}$ of 72±13 mg/kg, a two order of magnitude reduction in sedative-hypnotic potency compared to etomidate. The time required for righting reflexes to return after administering etomidate increased with the dose reaching 16.3±0.5 min at 3 mg/kg (the highest etomidate dose studied). In contrast, even after administering a 100 mg/kg dose of dimethoxy-etomidate, righting reflexes returned in 2.2±0.7 min, as shown in FIG. 3B.

Example 8. Suppression of Steroidogenesis by Etomidate and Dimethoxy-Etomidate

The in vivo adrenocortical inhibitory potencies of etomidate and dimethoxy-etomidate were assessed in dexamethasone-suppressed rats (four per group) immediately after administering vehicle alone, a low etomidate or dimethoxy-etomidate dose (0.3 mg/kg intravenous (IV)), an intermediate etomidate or dimethoxy-etomidate dose (3 mg/kg IV), or a high dimethoxy-etomidate dose (50 mg/kg) using an adrenocorticotropic hormone (ACTH)-stimulation test as previously described. Briefly, rats were pretreated with dexamethasone (0.2 mg/kg intravenously) to reduce endogenous ACTH production and minimize baseline adrenocortical steroid concentrations. Two hours later and after receiving a second dexamethasone dose, rats received ACTH1-24 (IV) and the desired dose of either etomidate or dimethoxy-etomidate solubilized in water containing a 1:1 molar ratio of Captisol (Ligand Pharmaceuticals, San Diego, Calif.) or water containing Captisol vehicle alone as a control. Fifteen minutes later, a blood sample was drawn and ACTH-stimulated adrenocortical steroid concentrations in the plasma were determined using enzyme-linked immunosorbent assays and a 96-well plate reader (Molecular Devices, Sunnyvale, Calif.).

Figures 4A, 4B, 4C, 4D, 4E, 4F, 4G, 4H:
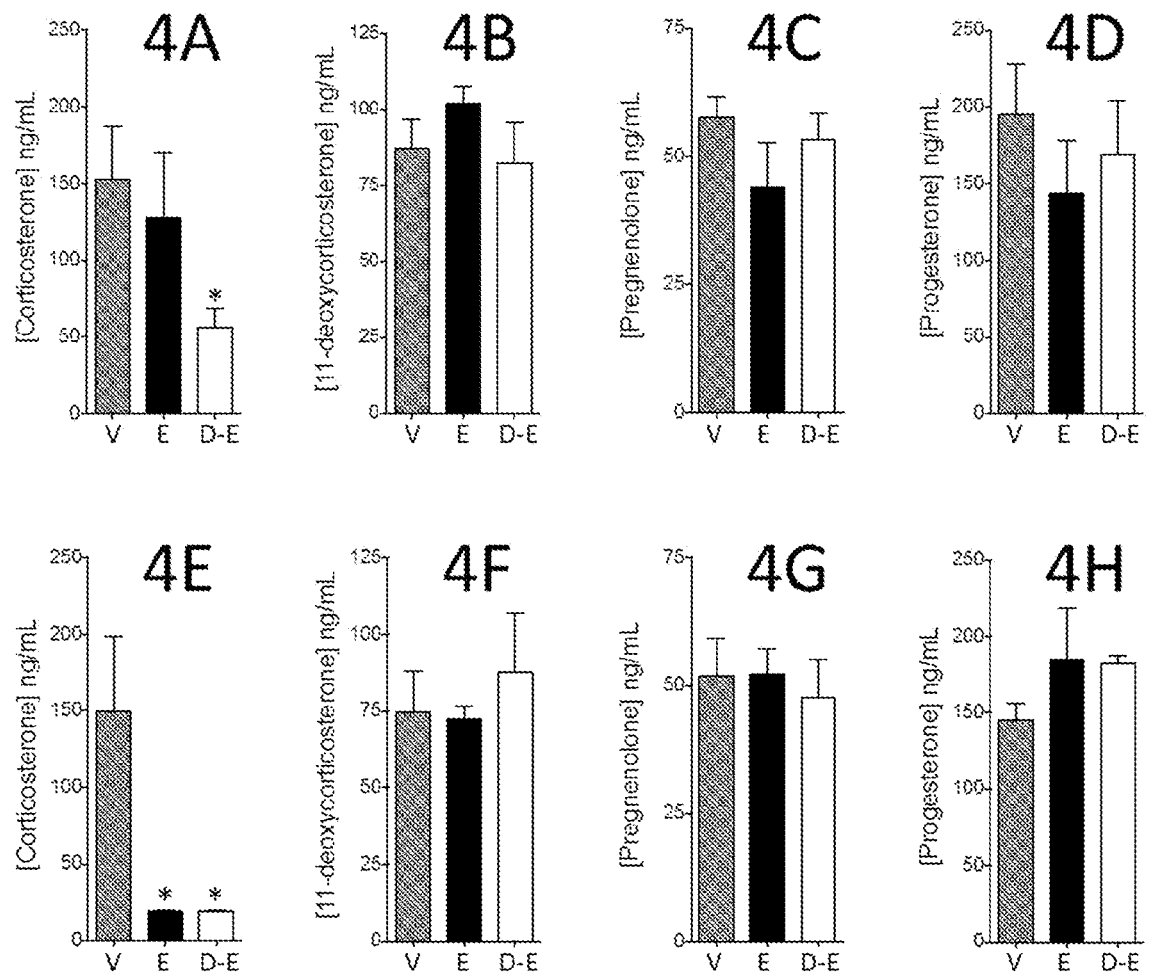
FIGS. 4A-4H show steroidogenesis inhibition produced by vehicle (V), etomidate (E), or dimethoxy-etomidate (D-E) in rats. Intravenous doses of etomidate and dimethoxy-etomidate were 0.3 mg/kg (FIGS. 4A-4D) or 3 mg/kg (FIGS. 4E-4H). Each bar represents the mean±SEM obtained from 4 rat experiments. *p<0.05.
Figures 5A, 5B, 5C, 5D:
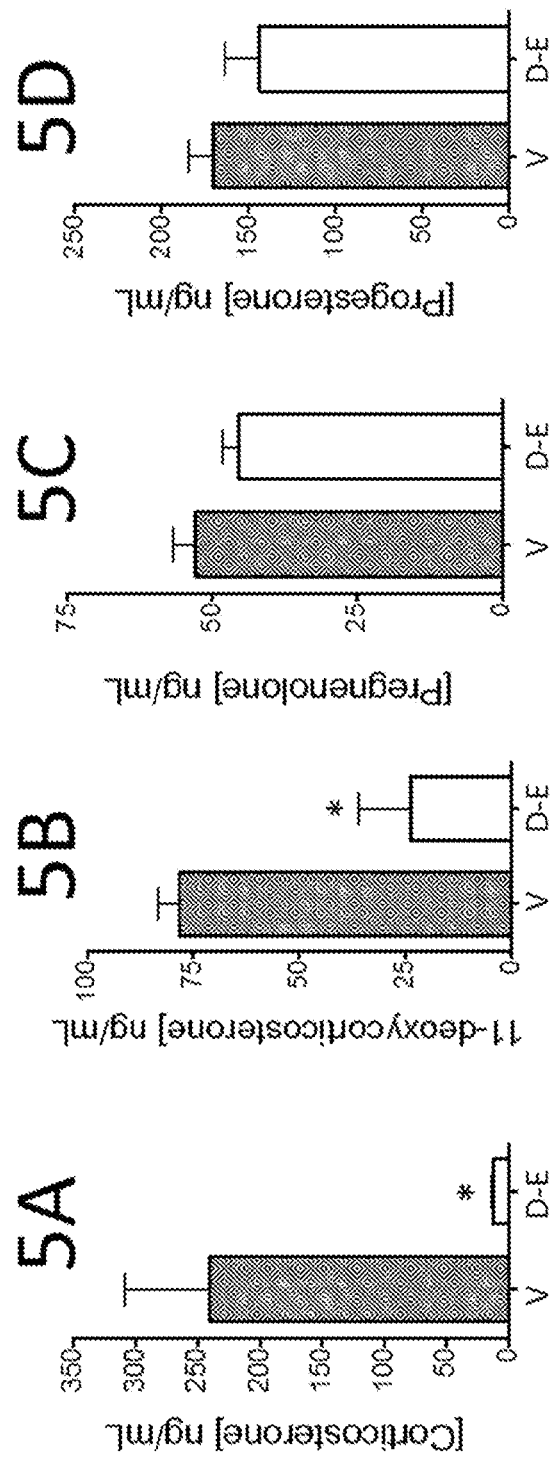
FIGS. 5A-5D show steroidogenesis inhibition produced by vehicle (V) or 50 mg/kg IV dimethoxy-etomidate in rats. Each bar represents the mean±SEM from 4 rat experiments. *p<0.05.
Figure 8:
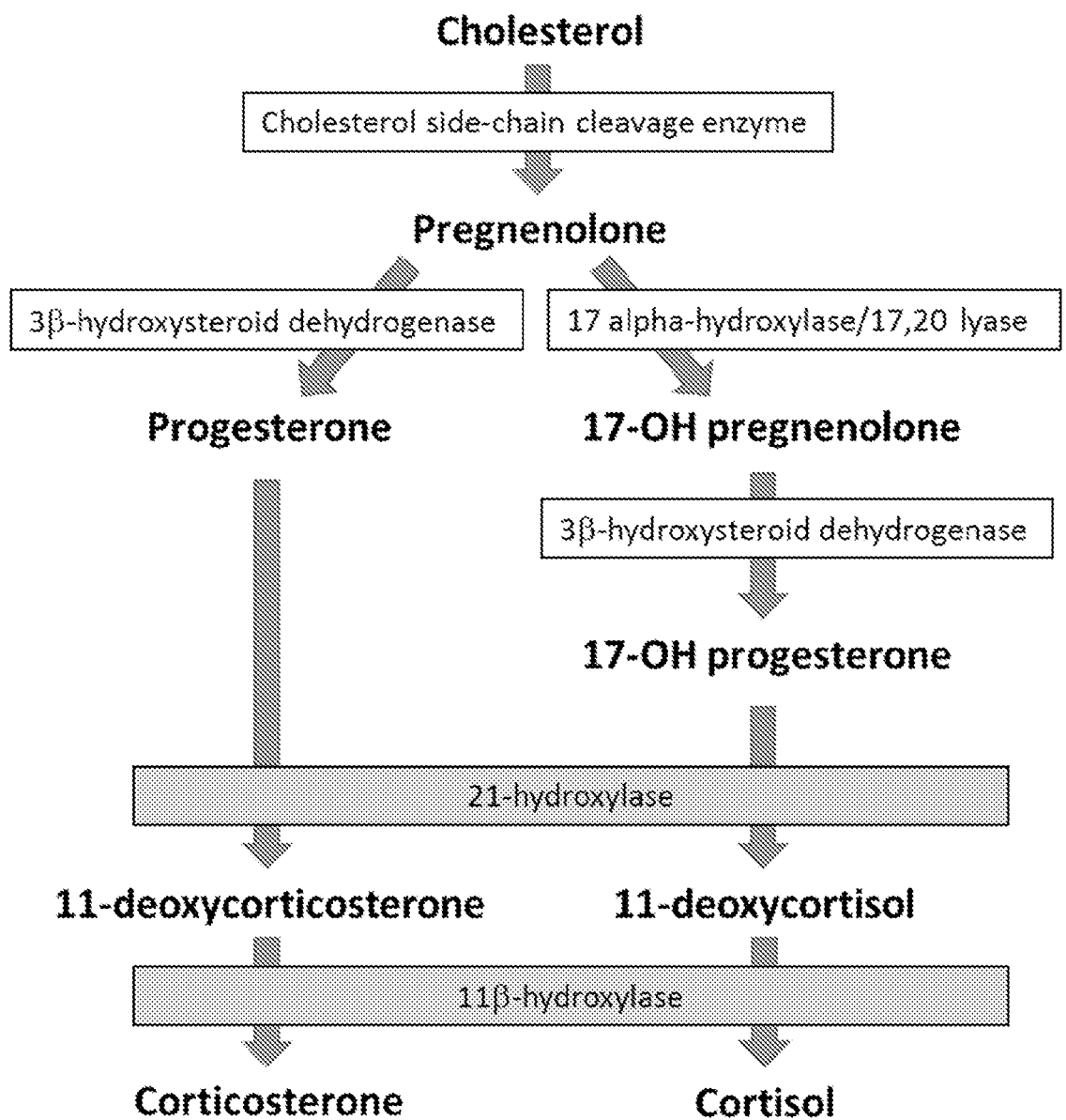
FIG. 8 shows a diagram representative of the adrenocortical steroid biosynthetic pathway. Etomidate and dimethoxy-etomidate inhibit 11β-hydroxylase most potently. With high doses, dimethoxy-etomidate also inhibits 21-hydroxylase.
Figure 10:
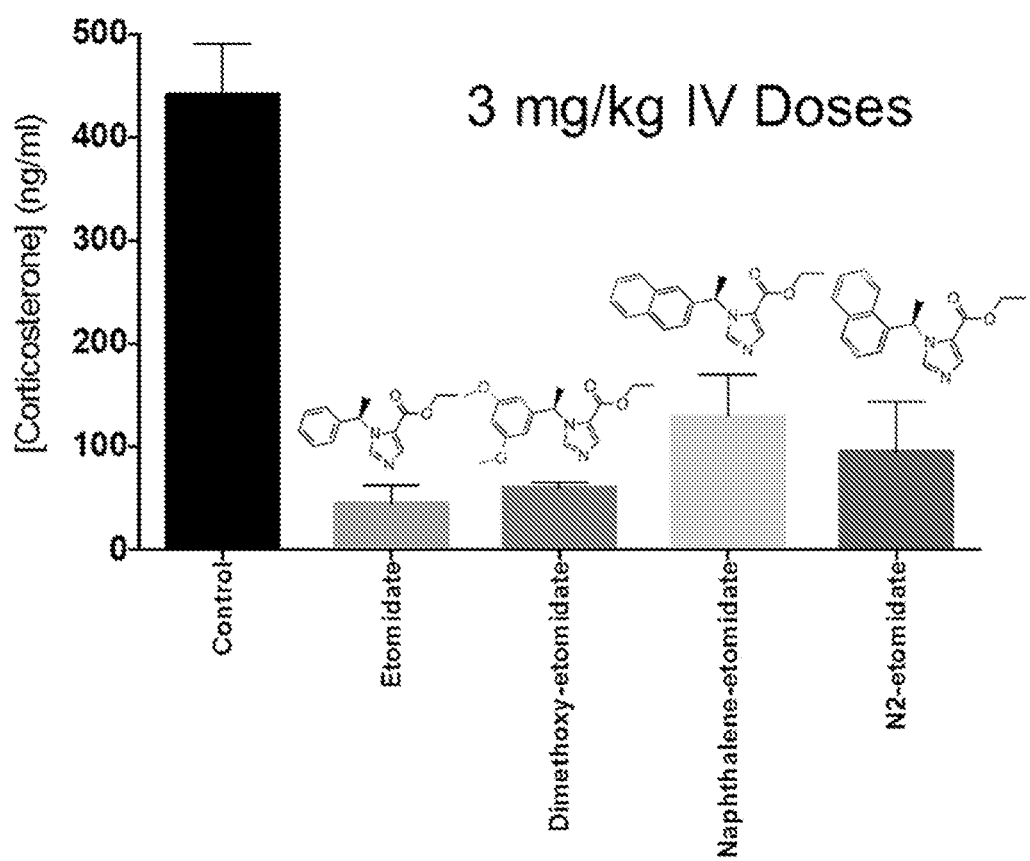
FIG. 10 shows steroidogenesis inhibition in rats (3 mg/kg IV dose) produced by vehicle, etomidate, the etomidate analogs of Examples 1, 4, and 5.

At an intravenous dose of 0.3 mg/kg, dimethoxy-etomidate reduced the ACTH-stimulated plasma corticosterone concentration by 63% from a control value of 152±35 ng/mL to 56±13 ng/mL whereas etomidate had no significant effect, as shown in FIG. 4A. At this dose, neither etomidate nor dimethoxy-etomidate altered the ACTH-stimulated plasma concentrations of 11-deoxycorticosterone (FIG. 4B), pregnenolone (FIG. 4C), or progesterone (FIG. 4D). At an intravenous dose of 3 mg/kg, both etomidate and dimethoxy-etomidate reduced the ACTH-stimulated plasma corticosterone concentrations by 87% from 150±48 ng/mL to respective values of 19±11 and 19±10 ng/m (FIG. 4E) without significantly affecting the ACTH-stimulated plasma concentrations of 11-deoxycorticosterone (FIG. 4F), pregnenolone (FIG. 4G), or progesterone (FIG. 4H). At a dose of 50 mg/kg, dimethoxy-etomidate reduced the ACTH-stimulated plasma corticosterone concentration by 95% from a control value of 240±69 ng/mL to 12±1 ng/mL (FIG. 5A) and the 11-deoxycorticosterone by 69% from 78±5 ng/mL to 24±12 ng/mL (FIG. 5B). The ACTH-stimulated plasma concentrations of pregnenolone (FIG. 5C) and progesterone (FIG. 5D) were unaffected by this high dimethoxy-etomidate dose. Etomidate was not studied at this high intravenous dose as it is lethal (see e.g, Pejo et al, *Anesthesiology*, 2014, 121:290-301). These studies show that ACTH-stimulated plasma concentrations of corticosterone were significantly reduced while those of its precursors (i.e., 11-deoxycorticosterone, pregnenolone, and progesterone) were unaffected. This pattern of steroidogenesis suppression indicates that 11β-hydroxylase is the most sensitive target of dimethoxy-etomidate in the adrenocortical steroid biosynthetic pathway, as shown in FIG. 8). As shown in FIG. 10, etomidate analogs with larger phenyl ring substituent groups (Examples 4-5) similarly inhibited adrenocortical steroid synthesis.

Example 9. Myoclonic Movements Produced by Etomidate and Dimethoxy-Etomidate

The abilities of the two drugs to produce myoclonus were assessed in Sprague-Dawley rats using a two-way crossover protocol. Each rat was randomized to receive either etomidate or dimethoxy-etomidate (3 mg/kg IV) solubilized in water containing a 1:1 molar ratio of Captisol. The desired drug was rapidly injected through a 24-gauge intravenous catheter placed in a tail vein followed by a 0.5-ml normal saline flush. Rats were immediately tested for LoRR and the number of myoclonic events was recorded during each 5-minute epoch for 30 minutes. A myoclonic event was defined as an unproductive (i.e., not associated with LoRR, feeding, or grooming behaviors) movement. Each distinct jerk or tremor constituted a single event. To avoid potentially confounding movements associated with bruxing, boggling, sniffing, and grooming, myoclonus was only considered to occur in the head and jaw when there was the presence of abnormal tongue lolling and jaw movement, or a sharp head movement out of sync with the rats breathing. At the end of the 30-minute observation period, rats were returned to their cages. After a 24-hour recovery period, each rat was crossed over to the other drug group and the experiment repeated.

Figure 6:
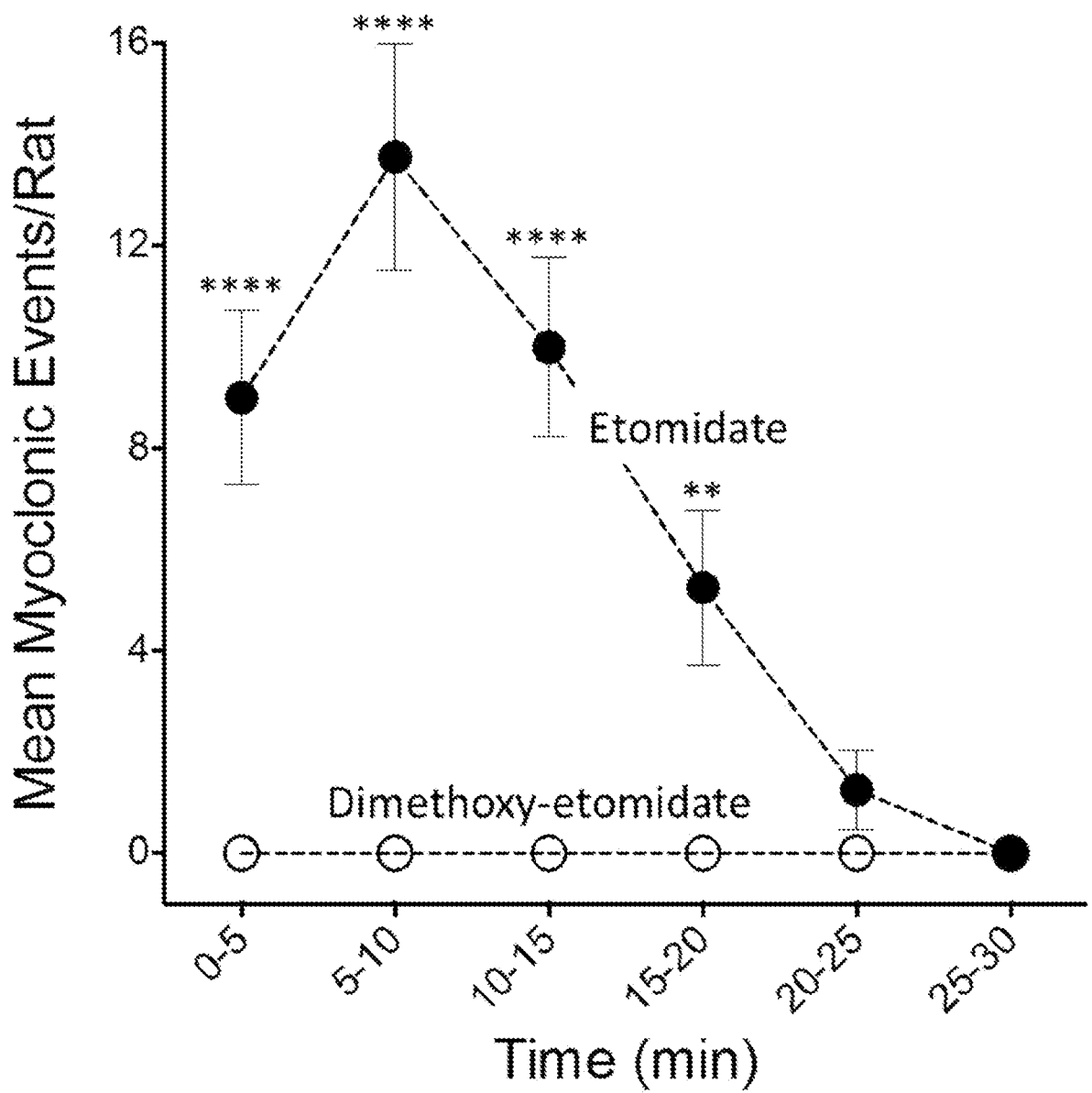
FIG. 6 shows myoclonic activity produced by etomidate and dimethoxy-etomidate in rats. Each rat was randomized to receive either etomidate or dimethoxy-etomidate (3 mg/kg IV). After drug administration, the number of myoclonic events observed during each 5-min epoch was recorded for 30 minutes. After 24 hours, the rat was switched to the other compound and the experiment was repeated. Each symbol represents the mean±SEM number of myoclonic events recorded from 8 rat experiments. p<0.01; **p<0.0001.

Etomidate (3 mg/kg IV) produced myoclonus and LORR in all rats (n=8). The mean (±SEM) total number of myoclonic events in each rat during the 30-minute observation period after etomidate administration was 34±2.4. The mean (±SEM) number of myoclonic events reached a maximum value of 13.8±2.2 per rat during the 5-10-minute epoch after administering the drug and then progressively decreased during the remaining 30-minute observation period, as shown in FIG. 6. In contrast, dimethoxy-etomidate (3 mg/kg IV) produced no myoclonic events or LoRR in any rat during the 30-minute observation period after drug administration.

Example 10. Displacement of [$^3$H]-Etomidate from Adrenal Membranes by Etomidate and Dimethoxy-Etomidate Adrenal glands from Sprague-Dawley rats were purchased from BioreclamationlVT (Baltimore, Md., USA), and prepared as previously described (see e.g., Pejo et al, *Anesthesiology*, 2016, 125:943-951). Briefly, 4 adrenal glands were thawed for each preparation, placed on a glass stand, cut into pieces, and then added to ice-cold preparation buffer (HEPES 10 mM, EDTA 1 mM, leupeptin 10 µg/mL, chymostatin 10 µg/mL, pepstatin A 10 µg/mL, aprotinin 2 µg/mL, polymethanesulfonyl fluoride 1 mM and ethanol 10 µg/mL). After homogenization, carboxylesterases were inactivated by incubating with 1 mM diisopropyl fluorophosphate (Sigma-Aldrich) for 60 min. The mixture was then centrifuged and the resulting pellet was washed twice. The final pellet was then re-suspended in buffer by manual homogenization, passed through a 23-gauge needle three times, aliquoted into 1 mL eppendorf tubes, and stored at −80° C. until used. The protein concentration in these samples was quantified using a Pierce BCA Protein Assay Kit (ThermoFisher, Rockford, Ill., USA). All binding experiments were performed in glass vials at room temperature with the final concentration of protein adjusted to 0.07 mg/mL. The reported data were obtained using 3 separate preparations.

After thawing, adrenal membranes were equilibrated for 30 min at room temperature with 2 nM [$^3$H]-etomidate along with ranging concentrations of etomidate or dimethoxy-etomidate (total volume 0.5 mL) in a 10 mM phosphate assay buffer (11.9 mM phosphates, 137 mM NaCl, 200 mM KCl, and 1 mM EDTA at pH=7.4). After equilibration, the mixture was passed through a pre-soaked (with 0.5% polyethylenimine in water for 2 h) 25 mm GF/B glass fiber filter under suction, the filter was immediately washed twice with 5 mL of assay buffer. After drying under a heat lamp for two hours, each filter was transferred to a scintillation vial. Liquiscint scintillation cocktail (National Diagnostics, Atlanta, Ga., USA) was added to the vial and the radioactivity in the vial quantified using a Packard Tri-Carb liquid scintillation counter (Meriden, Conn., USA). The concentration-response relationships for inhibition of [$^3$H]-etomidate by etomidate and dimethoxy-etomidate were fit to one and two site models, respectively, using Prism 6 for Mac OS X.

Previous reports have shown that [$^3$H]-etomidate binds specifically (i.e., etomidate-displacably), saturably, and reversibly to a single class of high affinity sites in adrenal homogenates (see e.g., Pejo et al, *Anesthesiology*, 2016, 125:943-951). The dissociation constant for this binding is within the range previously reported for etomidate inhibition of adrenocortical function in vitro and in vivo strongly suggesting that it reflects [$^3$H]-etomidate binding to 11β-hydroxylase (see e.g., Lamberts et al., *J. Pharmacol. Exp. Ther.*, 1987, 240:259-264; Crozier et al., Anaesthesist, 1988, 37:337-339; Cotten et al., *Anesthesiology*, 2010, 112:637-644; Campagna et al., *Anesthesiology*, 2014, 121:1203-1216).

Figure 7:
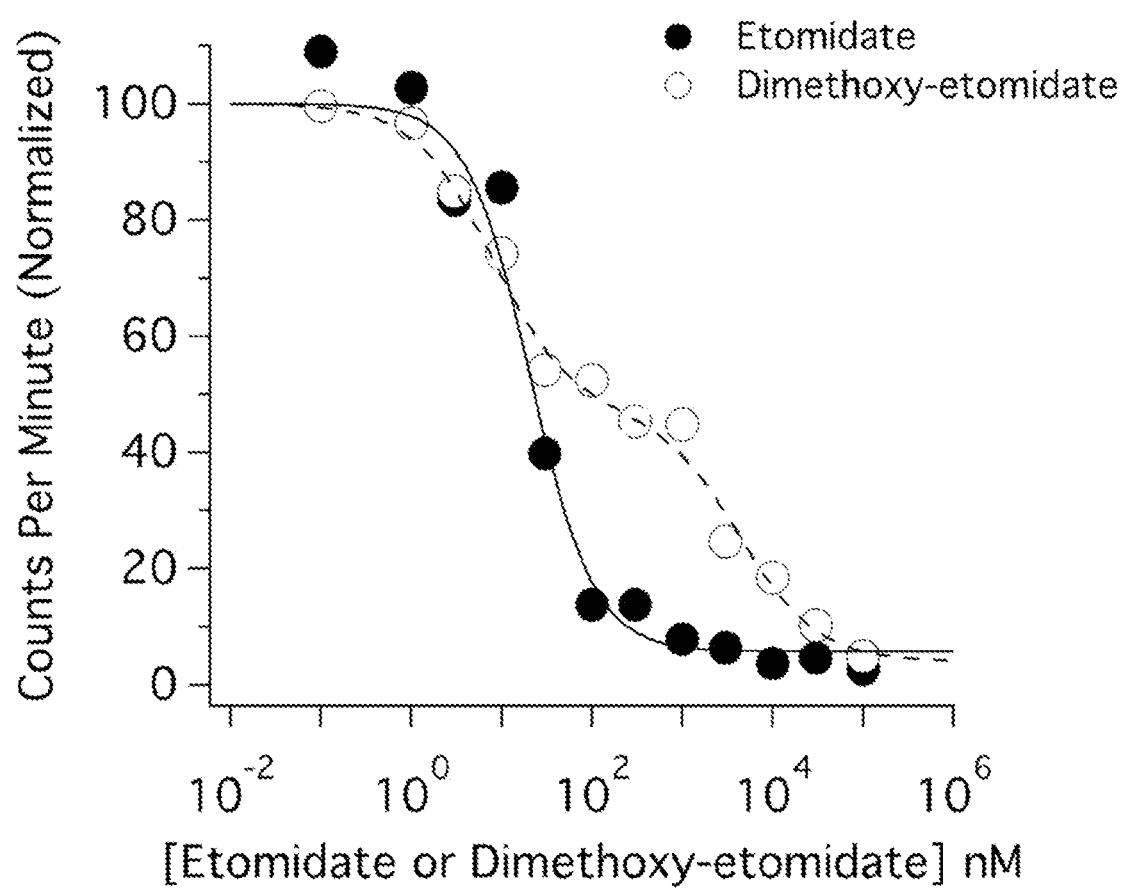
FIG. 7 shows displacement of [$^3$H]-etomidate by etomidate and dimethoxy-etomidate. [$^3$H]etomidate (2 nM) and the desired concentration of etomidate and dimethoxy-etomidate were equilibrated with membranes. The mixture was then filtered and radioactivity measured in the washed filter. Each data point is the mean±SEM (n=3) radioactivity measured in the washed filter. The standard errors are not visible in the graph because they were smaller than the data points. The curves show fits of each data set to a one site (etomidate) or two site (dimethoxy-etomidate) competitive binding equation. The half-inhibitory concentration ($IC_{50}$s) of etomidate was 21 nM (95% CI: 17-27 nM) whereas those for dimethoxy-etomidate were 7.9 nM (95% CI: 4.8-13 nM) and 4,270 nM (95% CI: 1,660-11,010 nM) with the high affinity site accounting for 55% (95% CI: 48-62%) of all sites.

To test whether etomidate and dimethoxy-etomidate bind to the same high affinity sites in adrenal homogenates, the ability to displace [$^3$H]-etomidate (2 nM) from these homogenates was compared. Both etomidate and dimethoxy-etomidate displaced [$^3$H]-etomidate from adrenal homogenates in a concentration-dependent manner, and at the highest concentration studied (100 M), both drugs displaced essentially all (≥95%) [$^3$H]-etomidate binding, as shown in FIG. 7. However, the concentration-dependence of this displacement differed between the two drugs. Displacement of [$^3$H]-etomidate by etomidate increased (i.e., [$^3$H]-etomidate binding decreased) in a monophasic manner indicative of a single class of high affinity sites whereas that by dimethoxy-etomidate increased in a biphasic manner, indicating the existence of two classes of binding sites having affinities that differ by orders of magnitude. An F-test was used to confirm this observation statistically and it was found that a one-site model was preferred for etomidate whereas a two-site one was preferred for dimethoxy-etomidate. Without being bound by theory, these non-identical sites (which may correspond to high and low affinity sites)—are believed to be overlapping and located within the active site 11β-hydroxylase. The $IC_{50}$ for the high affinity etomidate binding site was 21 nM (95% CI: 17-27 nM). The $IC_{50}$s for the high and low affinity dimethoxy-etomidate binding sites were 7.9 nM (95% CI: 4.8-13 nM) and 4,270 nM (95% CI: 1,660-11,010 nM) with the high affinity site accounting for 55% (95% CI: 48-62%) of all sites.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula Ia:

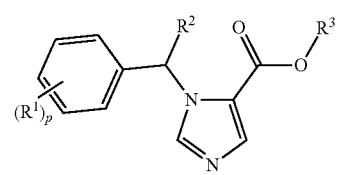

or a pharmaceutically acceptable salt thereof, wherein:
each $R^1$ is an independently selected $C_{1-6}$ alkoxy;
or, alternatively, two adjacent $R^1$ groups, together with the carbon atoms to which they are attached, form an aryl ring having 6 to 10 ring carbon atoms;
$R^2$ is $C_{1-4}$ alkyl;
$R^3$ is $C_{1-4}$ alkyl; and
p is 2 or 3.

2. The compound of claim 1, or a pharmaceutically acceptable salt thereof, wherein p is 2.

3. The compound of claim 1, or a pharmaceutically acceptable salt thereof, wherein each $R^1$ is methoxy.

4. The compound of claim 1, or a pharmaceutically acceptable salt thereof, wherein two adjacent $R^1$ groups, together with the carbon atoms to which they are attached, form an aryl ring having 6 to 10 ring carbon atoms.

5. The compound of claim 1, or a pharmaceutically acceptable salt thereof, wherein $R^2$ is methyl.

6. The compound of claim 1, or a pharmaceutically acceptable salt thereof, wherein $R^3$ is ethyl.

7. The compound of claim 1, wherein the compound of Formula I is a compound of Formula II:

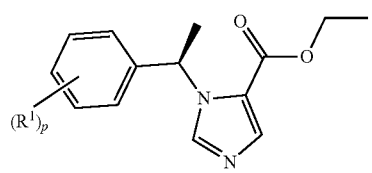

or a pharmaceutically acceptable salt thereof.

8. The compound of claim 1, or a pharmaceutically acceptable salt thereof, wherein the compound of Formula I is a compound of Formula III, Formula IV, Formula V, or Formula VI:

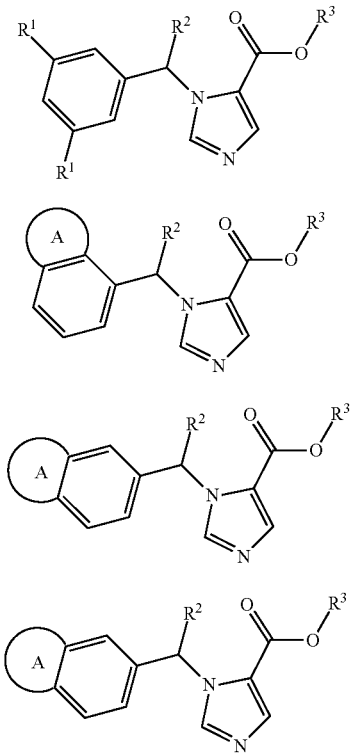

or a pharmaceutically acceptable salt thereof, wherein ring A is an aryl ring having 6 to 10 ring carbon atoms.

9. The compound of claim 1, wherein the compound of Formula I is selected from the group consisting of:

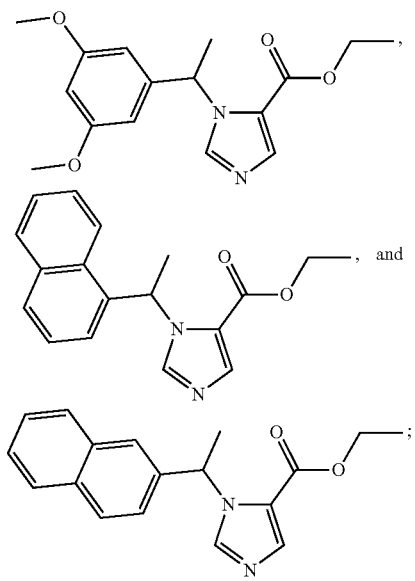

or a pharmaceutically acceptable salt thereof.

10. The compound of claim 1, wherein the compound of Formula I is selected from the group consisting of:

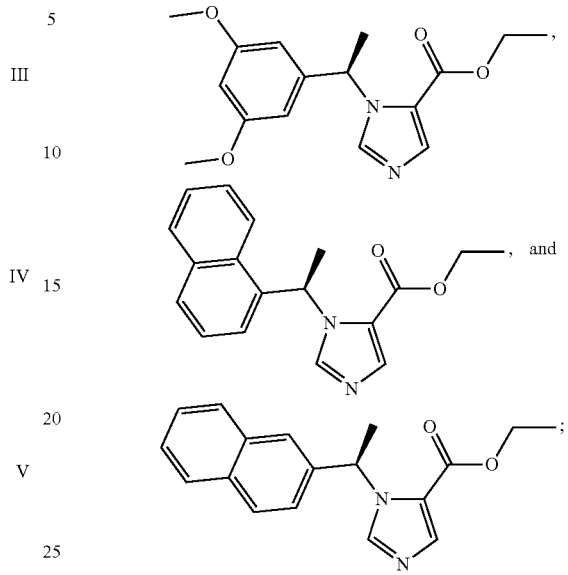

or a pharmaceutically acceptable salt thereof.

11. A pharmaceutical composition, comprising a compound of claim 1, or a pharmaceutically acceptable salt thereof, and at least one pharmaceutically acceptable carrier.

12. A method of inhibiting steroidogenesis in a subject, comprising administering to the subject a therapeutically effective amount of a compound of Formula I:

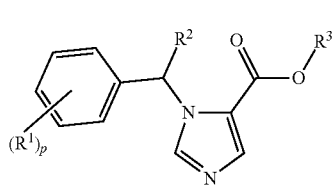

or a pharmaceutically acceptable salt thereof, wherein:
each $R^1$ is independently selected from the group consisting of halo and $C_{1-6}$ alkoxy;
or, alternatively, two adjacent $R^1$ groups, together with the carbon atoms to which they are attached, form an aryl ring having 6 to 10 ring carbon atoms;
$R^2$ is $C_{1-4}$ alkyl;
$R^3$ is $C_{1-4}$ alkyl; and
p is 1, 2, or 3.

13. A method of treating a disease associated with abnormal steroidogenesis in a subject, comprising administering to the subject a compound of Formula I:

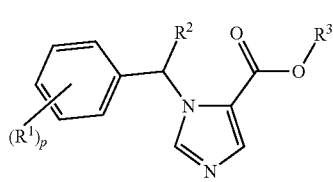

or a pharmaceutically acceptable salt thereof, wherein:
each $R^1$ is independently selected from the group consisting of halo and $C_{1-6}$ alkoxy;

or, alternatively, two adjacent $R^1$ groups, together with the carbon atoms to which they are attached, form an aryl ring having 6 to 10 ring carbon atoms;
$R^2$ is $C_{1-4}$ alkyl;
$R^3$ is $C_{1-4}$ alkyl; and
p is 1, 2, or 3.

14. The method of claim 13, wherein the disease is selected from the group consisting of Cushing's syndrome, hypercortisolemia, hypertension, diabetes, immunosuppression, water retention, depression, poor wound healing, fatigue, or any combination thereof.

15. The method of claim 13, wherein the therapeutically effective amount is an amount such that the subject does not exhibit a loss of righting reflex.

16. The method of claim 13, wherein the therapeutically effective amount is an amount such that the subject does not exhibit loss of consciousness.

17. The method of claim 13, wherein the therapeutically effective amount is an amount such that the subject does not exhibit loss of consciousness associated with enhanced receptor function of the GABAA receptor.

18. The method of claim 13, wherein the compound of Formula I is a compound of Formula Ia:

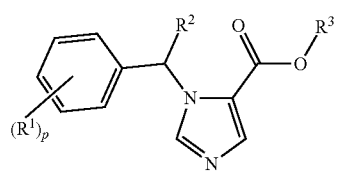

or a pharmaceutically acceptable salt thereof, wherein:
each $R^1$ is an independently selected $C_{1-6}$ alkoxy;
or, alternatively, two adjacent $R^1$ groups, together with the carbon atoms to which they are attached, form an aryl ring having 6 to 10 ring carbon atoms;
$R^2$ is $C_{1-4}$ alkyl;
$R^3$ is $C_{1-4}$ alkyl; and
p is 2 or 3.

19. The method of claim 13, wherein the compound is selected from the group consisting of:

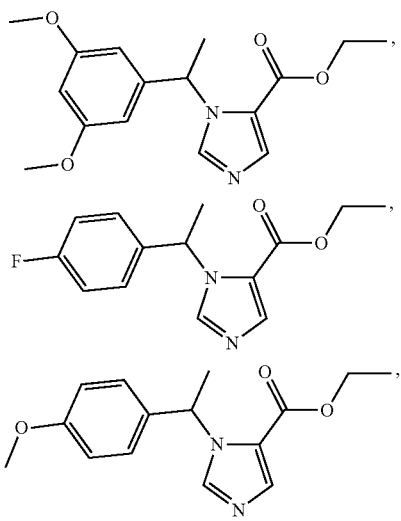

-continued

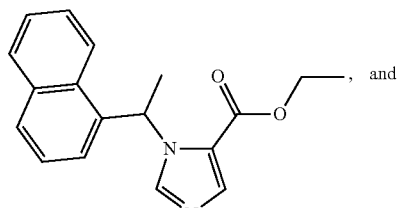

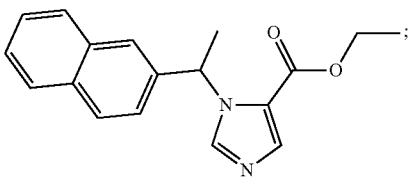

or a pharmaceutically acceptable salt thereof.

20. The method of claim 13, wherein the compound is selected from the group consisting of:

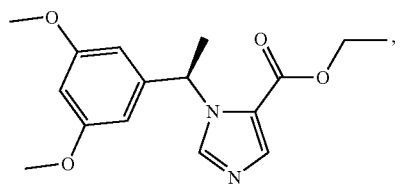

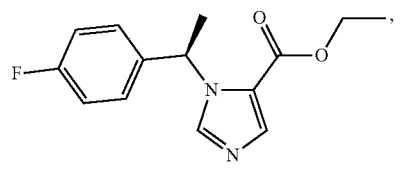

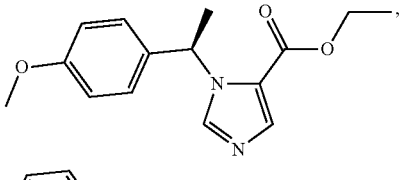

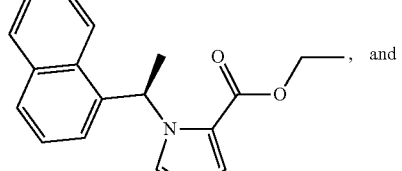

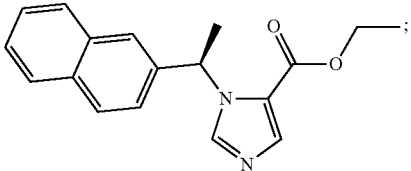

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,098,017 B2 | Page 1 of 1 |
| APPLICATION NO. | : 16/651248 | |
| DATED | : August 24, 2021 | |
| INVENTOR(S) | : Douglas Raines | |

It is certified that error appears in the above-identified patent and that said Letters Patent is hereby corrected as shown below:

On the Title Page

Column 2, item [56], Line 8, delete ""Cathoetomidate:" and insert -- "Carboetomidate: --

Column 2, item [56], Line 40, delete "Fly" and insert -- Fry --

In the Claims

Column 33, Line 20, Claim 17, delete "GABAA" and insert -- GABA$_A$ --

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*